United States Patent
Park et al.

(10) Patent No.: US 11,866,492 B2
(45) Date of Patent: Jan. 9, 2024

(54) ANTIBODY SPECIFICALLY BINDING TO FOLR1 AND USES THEREOF

(71) Applicant: ALTEOGEN, INC., Daejeon (KR)

(72) Inventors: Soon Jae Park, Daejeon (KR); Hye-Shin Chung, Daejeon (KR); Sunbae Lee, Daejeon (KR)

(73) Assignee: ALTEOGEN, INC., Daejeon (KR)

(*) Notice: Subject to any disclaimer, the term of this patent is extended or adjusted under 35 U.S.C. 154(b) by 492 days.

(21) Appl. No.: 16/980,074

(22) PCT Filed: Mar. 13, 2019

(86) PCT No.: PCT/KR2019/002911
§ 371 (c)(1),
(2) Date: Sep. 11, 2020

(87) PCT Pub. No.: WO2019/177372
PCT Pub. Date: Sep. 19, 2019

(65) Prior Publication Data
US 2021/0009685 A1    Jan. 14, 2021

(30) Foreign Application Priority Data
Mar. 14, 2018 (KR) .................. 10-2018-0029762

(51) Int. Cl.
| C07K 16/28 | (2006.01) |
| A61K 47/68 | (2017.01) |
| G01N 33/574 | (2006.01) |
| C07K 16/02 | (2006.01) |

(52) U.S. Cl.
CPC .......... *C07K 16/02* (2013.01); *A61K 47/6849* (2017.08); *G01N 33/57492* (2013.01); *C07K 2317/732* (2013.01); *C07K 2317/76* (2013.01); *C07K 2317/92* (2013.01); *G01N 2333/705* (2013.01)

(58) Field of Classification Search
CPC .............. C07K 16/28; C07K 2317/732; C07K 2317/76; C07K 2317/92; C07K 2317/55; C07K 2317/56; C07K 2317/565; A61K 47/6849; G01N 33/57492; G01N 2333/705
See application file for complete search history.

(56) References Cited

U.S. PATENT DOCUMENTS

| 11,235,065 B2* | 2/2022 | Park | A61P 35/00 |
| 2006/0239910 A1 | 10/2006 | Nicolaides et al. | |
| 2009/0274697 A1 | 11/2009 | Grasso et al. | |
| 2012/0164137 A1* | 6/2012 | Sass | C07K 16/28 435/69.6 |
| 2013/0183299 A1 | 7/2013 | O'Shannessy | |
| 2013/0189272 A1 | 7/2013 | Grasso et al. | |
| 2014/0205610 A1 | 7/2014 | Ando et al. | |
| 2017/0095571 A1 | 4/2017 | Ponte et al. | |

FOREIGN PATENT DOCUMENTS

| JP | 2008-500025 A | 1/2008 | |
| JP | 2008-508880 A | 3/2008 | |
| KR | 10-2015-0137015 A | 12/2015 | |
| WO | 95/24482 A1 | 9/1995 | |
| WO | 2011/106528 A1 | 9/2011 | |
| WO | 2012/119077 A1 | 9/2012 | |
| WO | 2016/079050 A1 | 5/2016 | |
| WO | 2016/114567 A1 | 7/2016 | |
| WO | WO-2017176007 A1 * | 10/2017 | A61K 31/337 |
| WO | 2019/177854 A1 | 9/2019 | |

OTHER PUBLICATIONS

Wolfgang Ebel et al., "Preclinical evaluation of MORAb-003, a humanized monoclonal antibody antagonizing folate receptor-alpha", Cancer Immunity, Mar. 9, 2007, 1-8 pgs., vol. 7.
Sun Ok Yoon et al., "Construction, Affinity Maturation, and Biological Characterization of an Anti-tumor-associated Glycoprotein-72 Humanized Antibody", The Journal of Biological Chemistry, Mar. 17, 2006, pp. 6985-6992, vol. 281, No. 11.
Gi-Hyeok Yang et al., "Affinity Maturation of an Anti-Hepatitis B Virus PreS1 Humanized Antibody by Phage Display", The Journal of Microbiology, Dec. 2007, p. 528-533, vol. 45, No. 6.
International Search Report for PCT/KR2019/002911 dated Jun. 18, 2019 (PCT/ISA/210).
Lin et al., "the antitumor activity of the human FOLR1-specific monoclonal antibody, farletuzumab, in an ovarian cancer mouse model is mediated by antibody-dependent cellular cytotoxicity", Cancer Biology & Therapy, 2013, vol. 14, Issue 11, pp. 1032-1038 (7 pages total).
Wei-Ping Yang et al.,"CDR Walking Mutagenesis for the Affinity Maturation of a Potent Human Anti-HIV-1 Antibody into the Picomolar Range", J. Mol. Biol., 1995, vol. 254, pp. 392-403 (13 pages total).

* cited by examiner

*Primary Examiner* — Hong Sang
*Assistant Examiner* — Francesca Edgingtongiordan
(74) *Attorney, Agent, or Firm* — Sughrue Mion, PLLC

(57) ABSTRACT

A modified antibody that binds specifically to folate receptor alpha (FOLR1) and blocks the activity of FOLR1 with an increased binding affinity, an antigen-binding fragment thereof, a composition containing the antibody or fragment, and their uses are disclosed. The modified antibody or antigen-binding fragment thereof may be used for the prevention or treatment of cancer proliferative disorder associated with an increased FOR1 expression, and may also be used for diagnosis of the disease. The proliferative disorder may be cancer.

10 Claims, 5 Drawing Sheets
Specification includes a Sequence Listing.

[Fig. 1]

```
                                      CDR-H1              CDR-H2
seq ID: 1   EVQLVESGGGVVQPGRSLRLSCSASGFTFSGYGLSWVRQAPGKGLEWVAMISSGGSYTYY
seq ID: 31  EVQLVESGGGVVQPGRSLRLSCSASGFTFSGYGLSWVRQAPGKGLEWVAMISSGGSYTYY
            ************************************************************
                                              CDR-H3
seq ID: 1   ADSVKGRFAISRDNAKNTLFLQMDSLRPEDTGVYFCARHGDPAWFAYWGQGTPVTVSSA
seq ID: 31  ADSVKGRFAISRDNAKNTLFLQMDSLRPEDTGVYFCARHGDVAWFAYWGQGTPVTVSSA
            ************************************** **************** seq ID: 1   STKGPSVFPLAPSSKSTSGGTAALGCLVKDYFPEPVTVSWNSGALTSGVHTFPAVLQSSG
seq ID: 31  STKGPSVFPLAPSSKSTSGGTAALGCLVKDYFPEPVTVSWNSGALTSGVHTFPAVLQSSG
            ************************************************************ seq ID: 1   LYSLSSVVTVPSSSLGTQTYICNVNHKPSNTKVDKKVEPKSCDKTHTCPPCPAPELLGGP
seq ID: 31  LYSLSSVVTVPSSSLGTQTYICNVNHKPSNTKVDKKVEPKSCDKTHTCPPCPAPELLGGP
            ************************************************************ seq ID: 1   SVFLFPPKPKDTLMISRTPEVTCVVVDVSHEDPEVKFNWYVDGVEVHNAKTKPREEQYNS
seq ID: 31  SVFLFPPKPKDTLMISRTPEVTCVVVDVSHEDPEVKFNWYVDGVEVHNAKTKPREEQYNS
            ************************************************************ seq ID: 1   TYRVVSVLTVLHQDWLNGKEYKCKVSNKALPAPIEKTISKAKGQPREPQVYTLPPSRDEL
seq ID: 31  TYRVVSVLTVLHQDWLNGKEYKCKVSNKALPAPIEKTISKAKGQPREPQVYTLPPSRDEL
            ************************************************************ seq ID: 1   TKNQVSLTCLVKGFYPSDIAVEWESNGQPENNYKTTPPVLDSDGSFFLYSKLTVDKSRWQ
seq ID: 31  TKNQVSLTCLVKGFYPSDIAVEWESNGQPENNYKTTPPVLDSDGSFFLYSKLTVDKSRWQ
            ************************************************************ seq ID: 1   QGNVFSCSVMHEALHNHYTQKSLSLSPGK
seq ID: 31  QGNVFSCSVMHEALHNHYTQKSLSLSPGK
            *****************************
```

[Fig. 2]

```
                                  CDR-L1                    CDR-L2
seq ID: 2   DIQLTQSPSSLSASVGDRVTITCSVSSISSNNLHWYQQKPGKAPKPWIYGTSNLASGVP
seq ID: 32  DIQLTQSPSSLSASVGDRVTITCSASSQLSSSYLHWYQQKPGKAPKPWIYGTSSRASGVP
seq ID: 33  DIQLTQSPSSLSASVGDRVTITCSASSQLSSSYLHWYQQKPGKAPKPWIYGTSSRASGVP
seq ID: 34  DIQLTQSPSSLSASVGDRVTITCSASSQLSSSYLHWYQQKPGKAPKPWIYGTSNLASGVP
seq ID: 35  DIQLTQSPSSLSASVGDRVTITCSVSSISSNNLHWYQQKPGKAPKPWIYGTSSRASGVP
            ********************** ** *** ********************  *****
                                         CDR-L3
seq ID: 2   SRFSGSGSGTDYTFTISSLQPEDIATYYCQQWSSYPYMYTFGQGTKVEIKRTVAAPSVFI
seq ID: 32  SRFSGSGSGTDYTFTISSLQPEDIATYYCQQWSSYPYMYTFGQGTKVEIKRTVAAPSVFI
seq ID: 33  SRFSGSGSGTDYTFTISSLQPEDIATYYCQQWSSYPYMYTFGQGTKVEIKRTVAAPSVFI
seq ID: 34  SRFSGSGSGTDYTFTISSLQPEDIATYYCQQWSSYPYMYTFGQGTKVEIKRTVAAPSVFI
seq ID: 35  SRFSGSGSGTDYTFTISSLQPEDIATYYCQQWSSYPYMYTFGQGTKVEIKRTVAAPSVFI
            ************************************************************ seq ID: 2   FPPSDEQLKSGTASVVCLLNNFYPREAKVQWKVDNALQSGNSQESVTEQDSKDSTYSLSS
seq ID: 32  FPPSDEQLKSGTASVVCLLNNFYPREAKVQWKVDNALQSGNSQESVTEQDSKDSTYSLSS
seq ID: 33  FPPSDEQLKSGTASVVCLLNNFYPREAKVQWKVDNALQSGNSQESVTEQDSKDSTYSLSS
seq ID: 34  FPPSDEQLKSGTASVVCLLNNFYPREAKVQWKVDNALQSGNSQESVTEQDSKDSTYSLSS
seq ID: 35  FPPSDEQLKSGTASVVCLLNNFYPREAKVQWKVDNALQSGNSQESVTEQDSKDSTYSLSS
            ************************************************************ seq ID: 2   TLTLSKADYEKHKVYACEVTHQGLSSPVTKSFNRGEC
seq ID: 32  TLTLSKADYEKHKVYACEVTHQGLSSPVTKSFNRGEC
seq ID: 33  TLTLSKADYEKHKVYACEVTHQGLSSPVTKSFNRGEC
seq ID: 34  TLTLSKADYEKHKVYACEVTHQGLSSPVTKSFNRGEC
seq ID: 35  TLTLSKADYEKHKVYACEVTHQGLSSPVTKSFNRGEC
            *************************************
```

[Fig. 3]
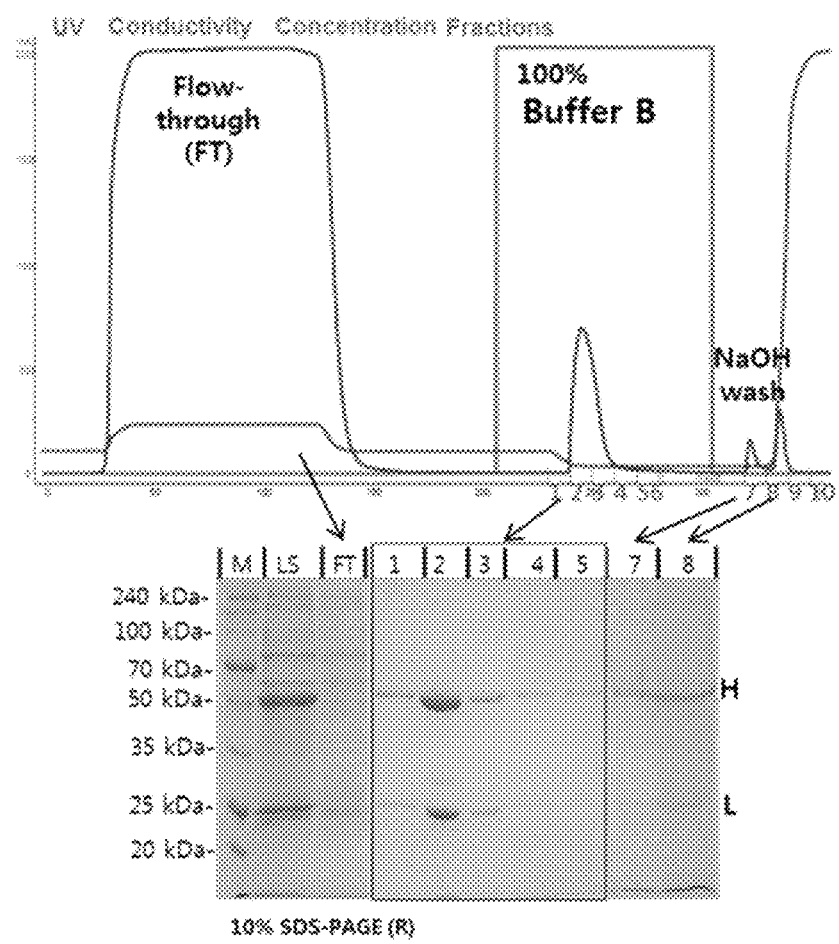

[Fig. 4]
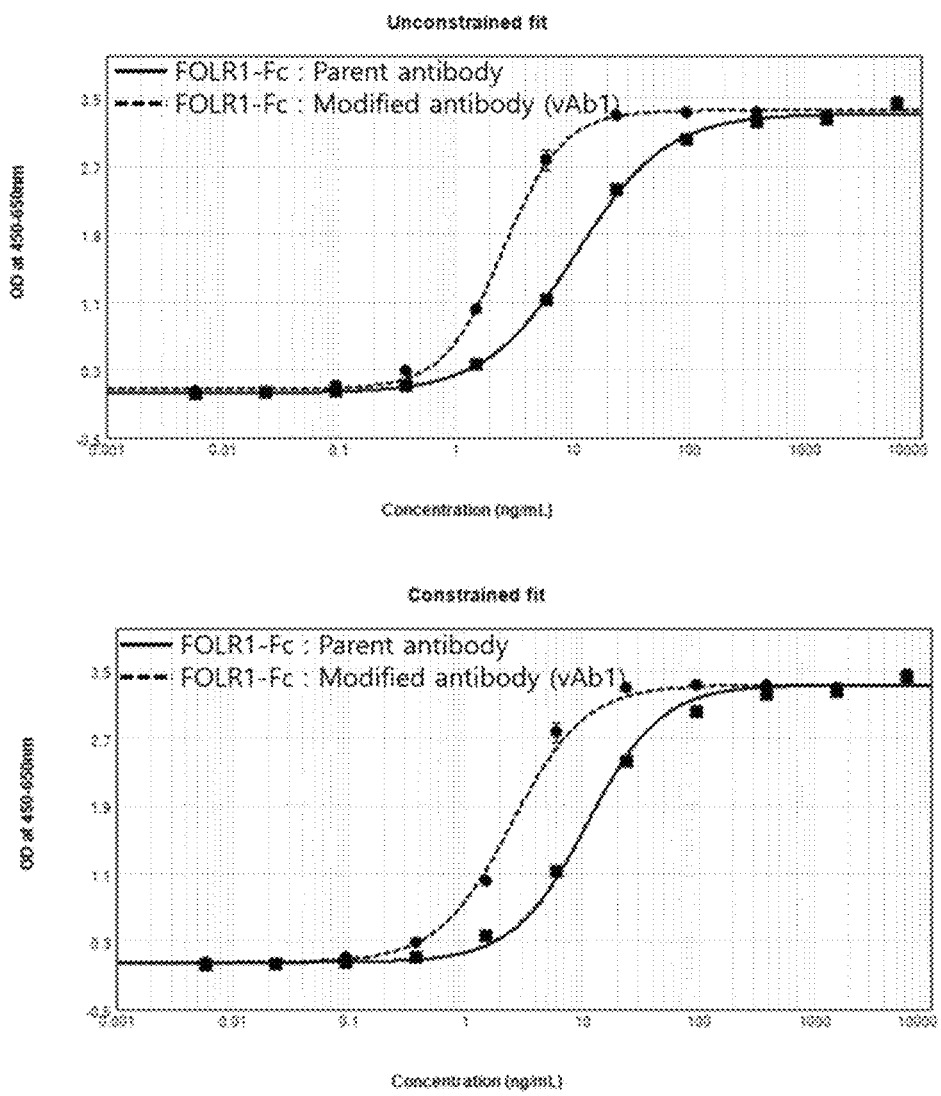

[Fig. 5]
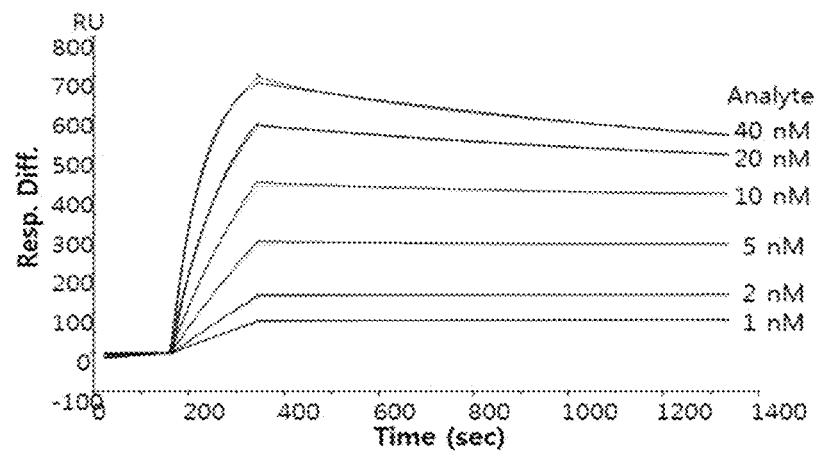
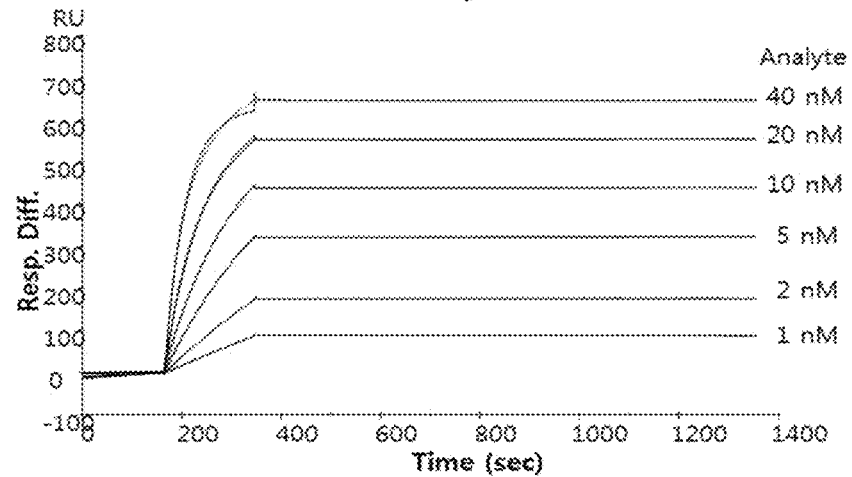

```
                              SEQUENCE LISTING

<160> NUMBER OF SEQ ID NOS: 54

<210> SEQ ID NO 1
<211> LENGTH: 119
<212> TYPE: PRT
<213> ORGANISM: Artificial Sequence
<220> FEATURE:
<223> OTHER INFORMATION: Heavy Chain

<400> SEQUENCE: 1

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115

<210> SEQ ID NO 2
<211> LENGTH: 110
<212> TYPE: PRT
<213> ORGANISM: Artificial Sequence
<220> FEATURE:
<223> OTHER INFORMATION: Light Chain

<400> SEQUENCE: 2

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys
            100                 105                 110

<210> SEQ ID NO 3
<211> LENGTH: 10
<212> TYPE: PRT
<213> ORGANISM: Artificial Sequence
<220> FEATURE:
<223> OTHER INFORMATION: CDR-H1

<400> SEQUENCE: 3
```

```
Gly Phe Thr Phe Ser Gly Tyr Gly Leu Ser
1               5                   10

<210> SEQ ID NO 4
<211> LENGTH: 15
<212> TYPE: PRT
<213> ORGANISM: Artificial Sequence
<220> FEATURE:
<223> OTHER INFORMATION: CDR-H2

<400> SEQUENCE: 4

Met Ile Ser Ser Gly Gly Ser Tyr Thr Tyr Tyr Ala Asp Ser Val
1               5                   10                  15

<210> SEQ ID NO 5
<211> LENGTH: 10
<212> TYPE: PRT
<213> ORGANISM: Artificial Sequence
<220> FEATURE:
<223> OTHER INFORMATION: CDR-H3

<400> SEQUENCE: 5

His Gly Asp Asp Pro Ala Trp Phe Ala Tyr
1               5                   10

<210> SEQ ID NO 6
<211> LENGTH: 12
<212> TYPE: PRT
<213> ORGANISM: Artificial Sequence
<220> FEATURE:
<223> OTHER INFORMATION: CDR-L1

<400> SEQUENCE: 6

Ser Val Ser Ser Ser Ile Ser Ser Asn Asn Leu His
1               5                   10

<210> SEQ ID NO 7
<211> LENGTH: 7
<212> TYPE: PRT
<213> ORGANISM: Artificial Sequence
<220> FEATURE:
<223> OTHER INFORMATION: CDR-L2

<400> SEQUENCE: 7

Gly Thr Ser Asn Leu Ala Ser
1               5

<210> SEQ ID NO 8
<211> LENGTH: 11
<212> TYPE: PRT
<213> ORGANISM: Artificial Sequence
<220> FEATURE:
<223> OTHER INFORMATION: CDR-L3

<400> SEQUENCE: 8

Gln Gln Trp Ser Ser Tyr Pro Tyr Met Tyr Thr
1               5                   10

<210> SEQ ID NO 9
<211> LENGTH: 55
<212> TYPE: DNA
<213> ORGANISM: Artificial Sequence
<220> FEATURE:
<223> OTHER INFORMATION: primer

<400> SEQUENCE: 9
```

```
gcctctggct tcactttcag trrttacgvt mtgarttggg tgagacaggc acctg      55
```

```
<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
actgaaagtg aagccagagg c                                          21

<210> SEQ ID NO 11
<211> LENGTH: 66
<212> TYPE: DNA
<213> ORGANISM: Artificial Sequence
<220> FEATURE:
<221> NAME/KEY: n is a or g or c or t
<222> LOCATION: (22)..(23)
<220> FEATURE:
<221> NAME/KEY: n is a or g or c or t
<222> LOCATION: (25)..(26)
<220> FEATURE:
<223> OTHER INFORMATION: primer

<400> SEQUENCE: 11
ggggtctatt tttgtgcaag annknnkgac gatccagcat ggtttgmtta ctggggccaa  60
gggacc                                                            66

<210> SEQ ID NO 12
<211> LENGTH: 66
<212> TYPE: DNA
<213> ORGANISM: Artificial Sequence
<220> FEATURE:
<221> NAME/KEY: n is a or g or c or t
<222> LOCATION: (25)..(26)
<220> FEATURE:
<221> NAME/KEY: is a or g or c or t
<222> LOCATION: (28)..(29)
<220> FEATURE:
<223> OTHER INFORMATION: primer

<400> SEQUENCE: 12
ggggtctatt tttgtgcaag acacnnknnk gatccagcat ggtttgmtta ctggggccaa  60
gggacc                                                            66

<210> SEQ ID NO 13
<211> LENGTH: 66
<212> TYPE: DNA
<213> ORGANISM: Artificial Sequence
<220> FEATURE:
<221> NAME/KEY: n is a or g or c or t
<222> LOCATION: (28)..(29)
<220> FEATURE:
<221> NAME/KEY: n is a or g or c or t
<222> LOCATION: (31)..(32)
<220> FEATURE:
<223> OTHER INFORMATION: primer

<400> SEQUENCE: 13
ggggtctatt tttgtgcaag acacggtnnk nnkccagcat ggtttgmtta ctggggccaa  60
gggacc                                                            66

<210> SEQ ID NO 14
<211> LENGTH: 66
<212> TYPE: DNA
<213> ORGANISM: Artificial Sequence
```

```
<220> FEATURE:
<221> NAME/KEY: n is a or g or c or t
<222> LOCATION: (31)..(232)
<220> FEATURE:
<221> NAME/KEY: n is a or g or c or t
<222> LOCATION: (34)..(35)
<220> FEATURE:
<223> OTHER INFORMATION: primer

<400> SEQUENCE: 14 gggtctatt tttgtgcaag acacggtgac nnknnkgcat ggtttgmtta ctggggccaa      60
gggacc                                                               66

<210> SEQ ID NO 15
<211> LENGTH: 66
<212> TYPE: DNA
<213> ORGANISM: Artificial Sequence
<220> FEATURE:
<221> NAME/KEY: n is a or g or c or t
<222> LOCATION: (34)..(35)
<220> FEATURE:
<221> NAME/KEY: n is a or g or c or t
<222> LOCATION: (37)..(38)
<220> FEATURE:
<223> OTHER INFORMATION: primer

<400> SEQUENCE: 15 gggtctatt tttgtgcaag acacggtgac gatnnknnkt ggtttgmtta ctggggccaa      60
gggacc                                                               66

<210> SEQ ID NO 16
<211> LENGTH: 66
<212> TYPE: DNA
<213> ORGANISM: Artificial Sequence
<220> FEATURE:
<221> NAME/KEY: n is a or g or c or t
<222> LOCATION: (37)..(38)
<220> FEATURE:
<221> NAME/KEY: n is a or g or c or t
<222> LOCATION: (40)..(41)
<220> FEATURE:
<223> OTHER INFORMATION: primer

<400> SEQUENCE: 16 gggtctatt tttgtgcaag acacggtgac gatccannkn nktttgmtta ctggggccaa      60
gggacc                                                               66

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
tcttgcacaa aaatagaccc c                                              21

<210> SEQ ID NO 18
<211> LENGTH: 75
<212> TYPE: DNA
<213> ORGANISM: Artificial Sequence
<220> FEATURE:
<223> OTHER INFORMATION: primer

<400> SEQUENCE: 18
acagagtcac catcacatgc agkgyttcct ccrgtvttag ttcaarcwat ctgmactggt     60
```

```
atcagcagaa gcccg                                                      75

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
gcatgtgatg gtgactctgt                                                 20

<210> SEQ ID NO 20
<211> LENGTH: 59
<212> TYPE: DNA
<213> ORGANISM: Artificial Sequence
<220> FEATURE:
<223> OTHER INFORMATION: primer

<400> SEQUENCE: 20
cccaaagccc tggatctacg vtrcctctav tckggmaast ggggtgcctt caaggttca     59

<210> SEQ ID NO 21
<211> LENGTH: 19
<212> TYPE: DNA
<213> ORGANISM: Artificial Sequence
<220> FEATURE:
<223> OTHER INFORMATION: primer

<400> SEQUENCE: 21
gtagatccag ggctttggg                                                  19

<210> SEQ ID NO 22
<211> LENGTH: 62
<212> TYPE: DNA
<213> ORGANISM: Artificial Sequence
<220> FEATURE:
<221> NAME/KEY: n is a or g or c or t
<222> LOCATION: (22)..(23)
<220> FEATURE:
<221> NAME/KEY: n is a or g or c or t
<222> LOCATION: (40)..(41)
<220> FEATURE:
<223> OTHER INFORMATION: primer

<400> SEQUENCE: 22
gcaacttact attgccagca gnnkbmtwat twtccaymtn nkymcacctt cggtcagggc    60
ac                                                                   62

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
ctgctggcaa tagtaagttg c                                               21

<210> SEQ ID NO 24
<211> LENGTH: 19
<212> TYPE: DNA
<213> ORGANISM: Artificial Sequence
<220> FEATURE:
<223> OTHER INFORMATION: primer

<400> SEQUENCE: 24
```

-continued

```
gcacgacagg tttcccgac                                              19
```

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25

```
aaccatcgat agcagcaccg                                             20
```

<210> SEQ ID NO 26
<211> LENGTH: 18
<212> TYPE: DNA
<213> ORGANISM: Artificial Sequence
<220> FEATURE:
<223> OTHER INFORMATION: primer

<400> SEQUENCE: 26

```
ggccatggct ggttgggc                                               18
```

<210> SEQ ID NO 27
<211> LENGTH: 18
<212> TYPE: DNA
<213> ORGANISM: Artificial Sequence
<220> FEATURE:
<223> OTHER INFORMATION: primer

<400> SEQUENCE: 27

```
gcccaaccag ccatggcc                                               18
```

<210> SEQ ID NO 28
<211> LENGTH: 10
<212> TYPE: PRT
<213> ORGANISM: Artificial Sequence
<220> FEATURE:
<223> OTHER INFORMATION: CDR-H3

<400> SEQUENCE: 28

His Gly Asp Asp Val Ala Trp Phe Ala Tyr
1               5                   10

<210> SEQ ID NO 29
<211> LENGTH: 12
<212> TYPE: PRT
<213> ORGANISM: Artificial Sequence
<220> FEATURE:
<223> OTHER INFORMATION: CDR-L1

<400> SEQUENCE: 29

Ser Ala Ser Ser Gly Leu Ser Ser Ser Tyr Leu His
1               5                   10

<210> SEQ ID NO 30
<211> LENGTH: 7
<212> TYPE: PRT
<213> ORGANISM: Artificial Sequence
<220> FEATURE:
<223> OTHER INFORMATION: CDR-L2

<400> SEQUENCE: 30

Gly Thr Ser Ser Arg Ala Ser
1               5

```
<210> SEQ ID NO 31
<211> LENGTH: 119
<212> TYPE: PRT
<213> ORGANISM: Artificial Sequence
<220> FEATURE:
<223> OTHER INFORMATION: Heavy Chain

<400> SEQUENCE: 31

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Val Ala Trp Phe Ala Tyr Trp Gly Gln Gly
            100                 105                 110

Thr Pro Val Thr Val Ser Ser
        115

<210> SEQ ID NO 32
<211> LENGTH: 110
<212> TYPE: PRT
<213> ORGANISM: Artificial Sequence
<220> FEATURE:
<223> OTHER INFORMATION: Light Chain

<400> SEQUENCE: 32

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Gly Leu Ser Ser Ser
            20                  25                  30

Tyr Leu His Trp Tyr Gln Gln Lys Pro Gly Lys Ala Pro Lys Pro Trp
        35                  40                  45

Ile Tyr Gly Thr Ser Ser Arg Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys
            100                 105                 110

<210> SEQ ID NO 33
<211> LENGTH: 110
<212> TYPE: PRT
<213> ORGANISM: Artificial Sequence
<220> FEATURE:
<223> OTHER INFORMATION: Light Chain

<400> SEQUENCE: 33

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Gly Leu Ser Ser Ser
            20                  25                  30
```

```
Tyr Leu His Trp Tyr Gln Gln Lys Pro Gly Lys Ala Pro Lys Pro Trp
            35                  40                  45

Ile Tyr Gly Thr Ser Asn Leu Ala Ser Gly Val Pro Ser Arg Phe Ser
 50                  55                  60

Gly Ser Gly Ser Gly Thr Asp Tyr Thr Phe Thr Ile Ser Ser Leu Gln
 65                  70                  75                  80

Pro Glu Asp Ile Ala Thr Tyr Tyr Cys Gln Gln Trp Ser Ser Tyr Pro
                 85                  90                  95

Tyr Met Tyr Thr Phe Gly Gln Gly Thr Lys Val Glu Ile Lys
            100                 105                 110

<210> SEQ ID NO 34
<211> LENGTH: 110
<212> TYPE: PRT
<213> ORGANISM: Artificial Sequence
<220> FEATURE:
<223> OTHER INFORMATION: Light Chain

<400> SEQUENCE: 34

Asp Ile Gln Leu Thr Gln Ser Pro Ser Ser Leu Ser Ala Ser Val Gly
 1               5                  10                  15

Asp Arg Val Thr Ile Thr Cys Ser Val Ser Ser Ile Ser Ser Asn
                 20                  25                  30

Asn Leu His Trp Tyr Gln Gln Lys Pro Gly Lys Ala Pro Lys Pro Trp
            35                  40                  45

Ile Tyr Gly Thr Ser Ser Arg Ala Ser Gly Val Pro Ser Arg Phe Ser
 50                  55                  60

Gly Ser Gly Ser Gly Thr Asp Tyr Thr Phe Thr Ile Ser Ser Leu Gln
 65                  70                  75                  80

Pro Glu Asp Ile Ala Thr Tyr Tyr Cys Gln Gln Trp Ser Ser Tyr Pro
                 85                  90                  95

Tyr Met Tyr Thr Phe Gly Gln Gly Thr Lys Val Glu Ile Lys
            100                 105                 110

<210> SEQ ID NO 35
<211> LENGTH: 12
<212> TYPE: PRT
<213> ORGANISM: Artificial Sequence
<220> FEATURE:
<223> OTHER INFORMATION: CDR-L1

<400> SEQUENCE: 35

Ser Ala Ser Ser Ser Leu Ser Ser Tyr Leu His
 1               5                  10

<210> SEQ ID NO 36
<211> LENGTH: 12
<212> TYPE: PRT
<213> ORGANISM: Artificial Sequence
<220> FEATURE:
<223> OTHER INFORMATION: CDR-L1

<400> SEQUENCE: 36

Arg Val Ser Ser Gly Ile Ser Ser Asn Asn Leu His
 1               5                  10

<210> SEQ ID NO 37
<211> LENGTH: 12
<212> TYPE: PRT
<213> ORGANISM: Artificial Sequence
<220> FEATURE:
```

<223> OTHER INFORMATION: CDR-L1

<400> SEQUENCE: 37

Arg Ala Ser Ser Gly Leu Ser Ser Asn Asn Leu His
1               5                   10

<210> SEQ ID NO 38
<211> LENGTH: 12
<212> TYPE: PRT
<213> ORGANISM: Artificial Sequence
<220> FEATURE:
<223> OTHER INFORMATION: CDR-L1

<400> SEQUENCE: 38

Arg Ala Ser Ser Gly Val Ser Ser Asn Asn Leu His
1               5                   10

<210> SEQ ID NO 39
<211> LENGTH: 12
<212> TYPE: PRT
<213> ORGANISM: Artificial Sequence
<220> FEATURE:
<223> OTHER INFORMATION: CDR-L1

<400> SEQUENCE: 39

Ser Ala Ser Ser Ser Ile Ser Ser Ser Tyr Leu His
1               5                   10

<210> SEQ ID NO 40
<211> LENGTH: 12
<212> TYPE: PRT
<213> ORGANISM: Artificial Sequence
<220> FEATURE:
<223> OTHER INFORMATION: CDR-L1

<400> SEQUENCE: 40

Ser Val Ser Ser Ser Leu Ser Ser Ser Asn Leu His
1               5                   10

<210> SEQ ID NO 41
<211> LENGTH: 7
<212> TYPE: PRT
<213> ORGANISM: Artificial Sequence
<220> FEATURE:
<223> OTHER INFORMATION: CDR-L2

<400> SEQUENCE: 41

Ala Thr Ser Ser Arg Ala Thr
1               5

<210> SEQ ID NO 42
<211> LENGTH: 7
<212> TYPE: PRT
<213> ORGANISM: Artificial Sequence
<220> FEATURE:
<223> OTHER INFORMATION: CDR-L2

<400> SEQUENCE: 42

Ala Thr Ser Asn Arg Glu Ser
1               5

<210> SEQ ID NO 43
<211> LENGTH: 7
<212> TYPE: PRT
<213> ORGANISM: Artificial Sequence
<220> FEATURE:
<223> OTHER INFORMATION: CDR-L2

```
<400> SEQUENCE: 43

Ala Thr Ser Ser Leu Ala Thr
1               5

<210> SEQ ID NO 44
<211> LENGTH: 7
<212> TYPE: PRT
<213> ORGANISM: Artificial Sequence
<220> FEATURE:
<223> OTHER INFORMATION: CDR-L2

<400> SEQUENCE: 44

Gly Ala Ser Ser Leu Ala Thr
1               5

<210> SEQ ID NO 45
<211> LENGTH: 7
<212> TYPE: PRT
<213> ORGANISM: Artificial Sequence
<220> FEATURE:
<223> OTHER INFORMATION: CDR-L2

<400> SEQUENCE: 45

Ala Thr Ser Asn Leu Ala Ser
1               5

<210> SEQ ID NO 46
<211> LENGTH: 7
<212> TYPE: PRT
<213> ORGANISM: Artificial Sequence
<220> FEATURE:
<223> OTHER INFORMATION: CDR-L2

<400> SEQUENCE: 46

Thr Ala Ser Ser Arg Ala Ser
1               5

<210> SEQ ID NO 47
<211> LENGTH: 7
<212> TYPE: PRT
<213> ORGANISM: Artificial Sequence
<220> FEATURE:
<223> OTHER INFORMATION: CDR-H3, CDR-L3H3

<400> SEQUENCE: 47

His Gly Asp Asp Pro Ala Trp
1               5

<210> SEQ ID NO 48
<211> LENGTH: 7
<212> TYPE: PRT
<213> ORGANISM: Artificial Sequence
<220> FEATURE:
<223> OTHER INFORMATION: CDR-H3, CDR-L3H3

<400> SEQUENCE: 48

His Gly Asp Asp Val Ala Trp
1               5

<210> SEQ ID NO 49
<211> LENGTH: 7
<212> TYPE: PRT
<213> ORGANISM: Artificial Sequence
<220> FEATURE:
<223> OTHER INFORMATION: CDR-H3
```

```
<400> SEQUENCE: 49

His Gly Asp Asp Ile Ala Trp
1               5

<210> SEQ ID NO 50
<211> LENGTH: 7
<212> TYPE: PRT
<213> ORGANISM: Artificial Sequence
<220> FEATURE:
<223> OTHER INFORMATION: CDR-L3H3

<400> SEQUENCE: 50

His Gly Asp Asp Ile Ser Trp
1               5

<210> SEQ ID NO 51
<211> LENGTH: 4
<212> TYPE: PRT
<213> ORGANISM: Artificial Sequence
<220> FEATURE:
<221> NAME/KEY: Xaa is any amino acid residue
<222> LOCATION: (2)..(2)
<220> FEATURE:
<221> NAME/KEY: Xaa is any amino acid residue
<222> LOCATION: (3)..(3)
<220> FEATURE:
<221> NAME/KEY: Xaa is any amino acid residue
<222> LOCATION: (4)..(4)
<220> FEATURE:
<223> OTHER INFORMATION: Synthetic construct

<400> SEQUENCE: 51

Cys Xaa Xaa Xaa

<210> SEQ ID NO 52
<211> LENGTH: 5
<212> TYPE: PRT
<213> ORGANISM: Artificial Sequence
<220> FEATURE:
<223> OTHER INFORMATION: Synthetic construct

<400> SEQUENCE: 52

Cys Gln Trp Val Ala
1               5

<210> SEQ ID NO 53
<211> LENGTH: 4
<212> TYPE: PRT
<213> ORGANISM: Artificial Sequence
<220> FEATURE:
<223> OTHER INFORMATION: Synthetic construct

<400> SEQUENCE: 53

Trp Gly Gln Gly
1

<210> SEQ ID NO 54
<211> LENGTH: 4
<212> TYPE: PRT
<213> ORGANISM: Artificial Sequence
<220> FEATURE:
<223> OTHER INFORMATION: Synthetic construct

<400> SEQUENCE: 54

Phe Gly Gln Gly
1
```

ANTIBODY SPECIFICALLY BINDING TO FOLR1 AND USES THEREOF

CROSS REFERENCE TO RELATED APPLICATIONS

This application is a national stage entry application of PCT/KR2019/002911 filed Mar. 13, 2019, which claims priority from Korean Patent Application No. 10-2018-0029762 filed Mar. 14, 2018.

TECHNICAL FIELD

The present invention relates to an antibody that binds specifically to folate receptor alpha (FOLR1) and blocks the activity of FOLR1, the antibody being a modified antibody having significantly increased binding affinity for an antigen compared to that of the parent antibody. More particularly, the present invention relates to an antibody or antigen-binding fragment thereof that binds specifically to FOLR1, an antibody-drug conjugate comprising the antibody or antigen-binding fragment thereof, a pharmaceutical composition for preventing or treating cancer comprising the same, and a composition for diagnosing disease comprising the same.

BACKGROUND ART

Folate receptor alpha (FOLR1) is a protein which is expressed at low to moderate levels in normal epithelial cells and is overexpressed in certain epithelial-derived cancers such as ovarian cancer, breast cancer, lung cancer, kidney cancer, colorectal cancer, and endometrial cancer. In particular, FOLR1 is overexpressed in more than 90% of ovarian cancer, and thus the antibodies that target FOLR1 are useful for the treatment of cancer (Sudimack and Lee, Adv. Drug Deliv. Rev. 2000, 41, 147-162). As a representative example of a therapeutic antibody, farletuzumab (MORAb-003) disclosed in US Patent Application Publication No. 2009/274697 (PCT International Publication No. 2005/080431) is a humanized monoclonal antibody. Farletuzumab was developed by Morphotek Inc., and has been reported as a potential therapeutic agent for ovarian cancer. Farletuzumab is known to bind to FOLR1 with a binding affinity corresponding to a KD value of about 2 nM (Grasso et al., Cancer Immun. 2007, 7, 6).

Typically, such therapeutic antibodies are extensively engineered to possess desirable biological and physicochemical properties, such as low immunogenicity, high affinity and specificity, optimal effector functions, and good solubility and stability. In particular, antibody humanization and affinity maturation are the most frequently applied engineering processes during the development of therapeutic antibody candidates. An antibody humanization method is a method of replacing a complementarity-determining region (CDR) of a non-human animal antibody with a CDR of a human antibody. Humanized antibodies resolve problems with non-human animal antibodies such as mouse antibodies, such as high immunogenicity, low effector function, and short blood half-life. By solving these problems, monoclonal antibodies have been developed as pharmaceuticals, and various humanized antibodies have already been approved for sale as therapeutic antibodies. Although these humanized antibodies actually show certain effects in clinical practice, it is also true that their binding affinities for antigens are lower than those of the original human antibodies, and that therapeutic antibodies having higher effects are required. Since these problems may arise due to the loss of affinity that results from direct grafting of murine CDRs onto a human framework acceptor sequence, mutations in CDRs or framework region (FR) residues supporting the structure of CDR loops are often necessary.

In this respect, the application of antibody engineering techniques to improve antibody efficacy is required. These techniques include an affinity maturation technique of increasing the affinity of an antibody for an antigen. Affinity maturation refers to a technique of increasing the binding affinity of an antibody for an antigen by introducing a random mutation into an antibody gene, and may be very useful for the development of new effective antibody drugs for therapeutic and diagnostic purposes. For in vitro affinity maturation, three approaches are typically used. These approaches include error-prone PCR, randomization of targeted residues using degenerate oligonucleotides, and chain shuffling. CDRs that may be selected as target residues are the logical target for randomization because CDR-H3 and CDR-L3 tend to dominate the antibody-antigen interaction. The binding affinity of an antibody is increased by changing the amino acids in the CDR region of the target antibody gene. It has been reported that, through this method, the binding affinity of AKA (a humanized antibody that binds to tumor-associated glycoprotein 72) was increased 22-fold by changing the amino acids in CDR-H3 of AKA (Hong et al., J. Biol. Chem. 2006, 281, 6985-6992), and the binding affinity of a developed antibody for hepatitis B virus antigen was also increased 6-fold (Hong el al., J. Microbiol. 2007, 45, 528-533).

A group of sequences having randomly arranged amino acids in the CDR region may be referred to as a library. Since antibodies coexist in the library, an operation of selecting antibodies from the library is required. One of the most effective technologies of selecting antibodies from the library is phage display technology. This technology is based on a direct linkage between phage phenotype and its encapsulated genotype, which leads to presentation of molecule libraries on the phage surface. Phage display is utilized in studying protein-ligand interactions and receptor binding sites and in improving or modifying the affinity of proteins for their binding partners.

Phage display involves the expression of selected proteins on the surface of a filamentous phage through fusion with a phage coat protein containing a genetic sequence that links a phenotype to genotype selection. When combined with antibody libraries, phage display allows for rapid in vitro selection of antigen-specific antibodies and recovery of coding sequences corresponding thereto. Large non-immune and synthetic human libraries have been constructed as well as smaller immune libraries based on capturing a single individual's immune repertoire. This completely in vitro process allows for isolation of antibodies against poorly immunogenic targets as well as those that cannot be obtained through animal immunization, thus further expanding the utility of the approach. Phage antibody display represents the first developed methodology for high-throughput screening for human therapeutic antibody candidates. Recently, other methods have been developed for generation of fully human therapeutic antibodies, such as single B-cell screening, next-generation genome sequencing and transgenic mice with human embryonic stem cell with hepatitis B genes. While each of these methods has particular advantages, phage display has remained a key methodology for human antibody discovery in terms of the ease and versatility of the screening method, because it is a process that is performed in vitro. In addition, panning, a method of selecting antibodies using phage display, refers to a process that comprises immobilizing an antigen on an immunotube and then adding an antibody library, displayed on the phage surface, to the immunotube, and selecting only bound antibodies through washing and elution processes. Phages carrying Fabs bound or not bound to the antigen are isolated by repeated washing. The antigen-bound phages are eluted off either through pH change or protease digestion and re-infected into E. coli, from which a new library enriched for antigen-binding clones can be made. After this process is repeated several times, the library can be sufficiently enriched so that the individual clones can be isolated from E. coli stock (expressed as monoclonal phage), tested and sequenced and the specific antibodies can be expressed.

Under this technical background, the present inventors have recognized that there is an urgent need to develop an antibody having excellent binding ability for FOLR1 to improve the efficacy of an antibody against FOLR1, and have invented an antibody having improved binding affinity for FOLR1 by introducing a mutation to the complementarity-determining region. In addition, the present inventors have constructed antibody libraries having amino acid mutations induced in the CDRs of the heavy-chain and light-chain variable regions of a parent antibody by affinity maturation, and have selected individual antibodies having increased binding affinity for FOLR1 by phage display technology, thereby completing the present invention.

The above information disclosed in this Background section is only for enhancement of understanding of the background of the present invention. Therefore, it may not contain information that forms a conventional art that is already known in the art to which the present invention pertains.

SUMMARY

An object of the present invention is to provide an antibody or antigen-binding fragment thereof that binds specifically to FOLR1 and an antibody having further improved binding affinity for an antigen compared to the above antibody.

Another object of the present invention is to provide an antibody-drug conjugate in which a drug is conjugated to the antibody or antigen-binding fragment thereof.

Still another object of the present invention is to provide a pharmaceutical composition for preventing or treating cancer comprising the antibody or antigen-binding fragment thereof or the antibody-drug conjugate.

Yet another object of the present invention is to provide a method for treating cancer comprising administering the antibody or antigen-binding fragment thereof or the antibody-drug conjugate.

Still yet another object of the present invention is to provide the use of the antibody or antigen-binding fragment thereof or the antibody-drug conjugate for treating cancer and the use of the antibody or antigen-binding fragment thereof or the antibody-drug conjugate in the manufacture of a medicament for treating cancer.

A further object of the present invention is to provide a composition for diagnosing disease comprising the antibody or antigen-binding fragment thereof or the antibody-drug conjugate, and a method for diagnosing disease using the antibody or antigen-binding fragment thereof or the antibody-drug conjugate.

To achieve the objects, an embodiment of the present invention provides an antibody or antigen-binding fragment thereof that binds specifically to folate receptor-α (FOLR1).

Preferably, the antibody or antigen-binding fragment thereof may comprise six complementarity-determining regions (CDRs), and the antibody or antigen-binding fragment thereof may comprise: a heavy-chain CDR1 of SEQ ID NO: 3, a heavy-chain CDR2 of SEQ ID NO: 4, and a heavy-chain CDR3 of SEQ ID NO: 5 or SEQ ID NO: 28; and a light-chain CDR1 of SEQ ID NO: 6 or SEQ ID NO: 29, a light-chain CDR2 of SEQ ID NO: 7 or SEQ ID NO: 30, and a light-chain CDR3 of SEQ ID NO: 8.

An embodiment of the present invention also provides an antibody-drug conjugate comprising the antibody or antigen-binding fragment thereof.

Another embodiment of the present invention also provides a pharmaceutical composition for preventing or treating cancer, the pharmaceutical composition comprising the antibody or antigen-binding fragment thereof or the antibody-drug conjugate.

Still another embodiment of the present invention also provides a method for treating cancer, the method comprising administering the antibody or antigen-binding fragment thereof or the antibody-drug conjugate.

An embodiment of the present invention also provides the use of the antibody or antigen-binding fragment thereof or the antibody-drug conjugate for treating cancer and the use of the antibody or antigen-binding fragment thereof or the antibody-drug conjugate in the manufacture of a medicament for treating cancer.

Another embodiment of the present invention also provides a composition for diagnosing disease comprising the antibody or antigen-binding fragment thereof or the antibody-drug conjugate, and a method for diagnosing disease using the antibody or antigen-binding fragment thereof or the antibody-drug conjugate.

BRIEF DESCRIPTION OF DRAWINGS

FIG. 1 shows a comparison of the heavy-chain variable region sequence of a parent antibody with that of a modified antibody. In FIG. 1, matches between the sequences are marked with asterisks, and one amino acid in the sequence of the CDR-H3 region is different between the two antibodies.

FIG. 2 shows a comparison of the light-chain variable region sequence of a parent antibody with that of a modified antibody. In FIG. 2, matches between the sequences are marked with asterisks, and the amino acid sequences of the CDR-L1 and CDR-L2 regions are different between the two antibodies.

FIG. 3 shows the results of fractionating a modified antibody by column purification using affinity resin chromatography, and shows a chromatogram and the results of SDS-PAGE analysis of each fraction (M: marker, LS: loading sample, H: heavy chain, L: light chain, R: reducing condition).

FIG. 4 shows the results of ELISA that indicate the binding affinity of each of a parent antibody and a modified antibody for FOLR1 as a function of concentration.

FIG. 5 shows the results of SPR analysis performed to compare the binding affinity of a parent antibody for FOLR1 with the binding affinity of a modified antibody for FOLR1.

DETAILED DESCRIPTION AND PREFERRED EMBODIMENTS OF THE INVENTION

Unless otherwise defined, all technical and scientific terms used in the present specification have the same meanings as commonly understood by those skilled in the art to which the present disclosure pertains. In general, the nomenclature used in the present specification is well known and commonly used in the art.

The term "antigen-binding fragment of an antibody" or "antibody fragment" refers to a fragment having an antigen-binding function, and includes Fab, F(ab'), F(ab')2 and Fv. Among antibody fragments, Fab is a structure having light-chain and heavy-chain variable regions, a light-chain constant region and a first heavy-chain constant region (CH1), and has one antigen-binding site. Fab' differs from Fab in that it has a hinge region containing at least one cysteine residue at the C-terminus of the heavy-chain CH1 region. An F(ab')2 antibody has a disulfide bond formed by cysteine residues in the hinge region of Fab'. Fv is a minimal antibody fragment having only a heavy-chain variable region and a light-chain variable region, and recombinant techniques of producing Fv fragments are disclosed in PCT International Patent Publication Nos. WO 88/10649, WO 88/106630, WO 88/07085, WO 88/07086, and WO 88/09344.

The variable regions of the antibody used in the present invention include three CDRs (CDR-H1, CDR-H2 and CDR-H3) in the heavy-chain portion of the antibody and include three CDRs (CDR-L1, CDR-L2 and CDR-L3) in the light-chain portion of the antibody. These regions all form a loop and are regions that bind specifically to an antigen.

In one aspect, the present invention is directed to an antibody or antigen-binding fragment thereof that binds specifically to folate receptor-α (FOLR1).

In an aspect of the present invention, the antibody or antigen-binding fragment thereof may inhibit the biological activity of folate receptor-α. Furthermore, the antibody or antigen-binding fragment thereof may induce antibody-dependent cellular cytotoxicity against cells that express folate receptor-α. In addition, the antibody or antigen-binding fragment thereof may have a dissociation constant of $1\times10^{-7}$ M or less for folate receptor-α.

As used herein, the term "parent antibody" refers to an anti-FOLR1 antibody that binds specifically to FOLR1. In the present invention, the antibody applied in a previous patent application (US2005/0232919 A1) was used as the parent antibody. The "parent antibody" in the present specification is one of the antibodies specified in the previous patent application, and has a heavy-chain sequence corresponding to SEQ ID NO: 1 below and a light-chain sequence corresponding to SEQ ID NO: 2 below:

```
Heavy chain
                                           (SEQ ID NO: 1)
EVQLVESGGGVVQPGRSLRLSCSASGFTFSGYGLSWVRQAPGKGLEWVAM

ISSGGSYTYYADSVKGRFAISRDNAKNTLFLQMDSLRPEDTGVYFCARHG

DDPAWFAYWGQGTPVTVSS

Light chain
                                           (SEQ ID NO: 2)
DIQLTQSPSSLSASVGDRVTITCSVSSSISSNNLHWYQQKPGKAPKPWIY

GTSNLASGVPSRFSGSGSGTDYTFTISSLQPEDIATYYCQQWSSYPYMYT

FGQGTKVEIK
```

The scope of the present invention includes not only a full-length antibody (full-length IgG) that binds specifically to FOLR1, but also an antigen-binding fragment (fragmented IgG) of the antibody molecule. The parent antibody used in the present invention comprises CDRs represented by sequences of SEQ ID NOs: 3 to 8.

Therefore, in embodiments of the present invention, the antibody or antigen-binding fragment thereof may comprise: the heavy-chain CDR1 of SEQ ID NO: 3; the heavy-chain CDR2 of SEQ ID NO: 4; the heavy-chain CDR3 of SEQ ID NO: 5; the light-chain CDR1 of SEQ ID NO: 6; the light-chain CDR2 of SEQ ID NO: 7; and the light-chain CDR3 of SEQ ID NO: 8.

In an aspect of the present invention, a CDR library based on the parent antibody was constructed as mentioned in PCT International Patent Publication No. WO2016/114567DP, and a pComb3X vector having the constructed library gene introduced therein is a phagemid vector, which is a plasmid DNA having a phage origin of replication and includes the phage surface protein pIII. The library gene is ligated to the 5' end of the pIII gene and expressed as a fusion protein in *E. coli*. VCSM13 helper phage is a phage that provides necessary genetic information so that a phagemid is assembled into a phage particle. The VCSM13 helper phage contains the kanamycin antibiotic resistance gene so that *E. coli* infected with the helper phage may be selected.

In addition, panning refers to a process of selectively amplifying only clones, which bind to a specific molecule, from a library of proteins, such as antibodies, displayed on the phage surface. The procedure comprises: adding a phage library to a target molecule immobilized on the surface to induce binding; removing unbound phage clones by washing; eluting only bound phage clones; re-infecting *E. coli* with the eluted phage clones; and amplifying target-bound phage clones using helper phages. By repeating this procedure, target-bound phage clones having a high binding affinity for the target molecule immobilized on the surface are selectively amplified.

As used herein, the term "modified antibody" refers to an antibody made by modifying the parent antibody. The present invention also provides a method for isolating and purifying the modified antibody. A culture obtained by culturing under conditions where the antibody protein is produced may be centrifuged to remove impurities, and the resulting material may be purified using affinity chromatography.

In addition, the modified antibody of an embodiment of the present invention has binding affinity for FOLR1. The binding affinity for FOLR1 may be measured using ELISA assay, SPR (surface plasmon resonance) assay, or the like. Specifically, the binding affinity may be measured by reacting an antibody composition with FOLR1 immobilized on a plate at various concentrations, additionally reacting a labeled antibody that recognizes the antibody, and calculating the concentration of the antibody composition bound to FOLR1. Thereby, it was possible to confirm that the binding ability of the antibody obtained from multiple-CDR libraries was improved more than that of the antibody obtained from single-CDR libraries.

In an embodiment of the present invention, the modified antibody may comprise the heavy-chain CDR3 of SEQ ID NO: 28, the light-chain CDR1 of SEQ ID NO: 29, or the light-chain CDR2 of SEQ ID NO: 30, which is a sequence modified from the parent antibody.

Therefore, in an embodiment of the present invention, the antibody or antigen-binding fragment thereof may comprise: the heavy-chain CDR1 of SEQ ID NO: 3; the heavy-chain CDR2 of SEQ ID NO: 4; the heavy-chain CDR3 of SEQ ID NO: 5 or SEQ ID NO: 28; the light-chain CDR1 of SEQ ID NO: 6 or SEQ ID NO: 29; the light-chain CDR2 of SEQ ID NO: 7 or SEQ ID NO: 30; and the light-chain CDR3 of SEQ ID NO: 8.

In an aspect of the present invention, the antibody or antigen-binding fragment thereof may comprise: a heavy-chain variable region of SEQ ID NO: 1 or SEQ ID NO: 31; and a light-chain variable region selected from the group consisting of SEQ ID NO: 2 and SEQ ID NOs: 32 to 34. Preferably, the antibody or antigen-binding fragment thereof may comprise: the heavy-chain variable region of SEQ ID NO: 1 and the light-chain variable region of SEQ ID NO: 32; the heavy-chain variable region of SEQ ID NO: 1 and the light-chain variable region of SEQ ID NO: 33; the heavy-chain variable region of SEQ ID NO: 1 and the light-chain variable region of SEQ ID NO: 34; the heavy-chain variable region of SEQ ID NO: 31 and the light-chain variable region of SEQ ID NO: 2; or the heavy-chain variable region of SEQ ID NO: 31 and the light-chain variable region of SEQ ID NO: 32.

In another aspect, the present invention is directed to an antibody-drug conjugate (ADC) in which a drug is conjugated to the antibody or antigen-binding fragment thereof.

With regard to the antibody-drug conjugate (ADC), the anticancer drug should remain stably bound to the antibody until the anticancer drug is delivered to the target cancer cell. The drug delivered to the target should be released from the antibody and induce apoptosis of the target cell. To this end, the drug should stably bind to the antibody, and at the same time, should exhibit sufficient cytotoxicity to induce apoptosis of the target cells when released in the target cell.

In an embodiment of the present invention, the antibody or antigen-binding fragment thereof and a cytotoxic substance comprising a drug such as an anticancer agent are bound to each other (via, for example, a covalent bond, a peptide bond or the like), and thus may be used as a conjugate or a fusion protein (when a cytotoxic substance and/or labeling substance (marker) is protein). The cytotoxic substance may be any substance which is toxic to cancer cells, particularly solid cancer cells, and may be at least one selected from the group consisting of radioisotopes, cytotoxic compounds (small molecules), cytotoxic proteins, and anticancer drugs, but is not limited thereto. The cytotoxic protein may be at least one selected from the group consisting of ricin, saporin, gelonin, momordin, deBouganin, diphtheria toxin, *pseudomonas* toxin, and the like, but is not limited thereto. The radioisotope may be at least one selected from the group consisting of $^{131}$I, $^{188}$Rh and $^{90}$Y, but is not limited thereto. The cytotoxic compound may be at least one selected from the group consisting of duocarmycin, monomethyl auristatin E (MMAE), monomethyl auristatin F (MMAF), N2'-diacetyl-N2'-(3-mercapto-1-oxopropyl) maytansine (DM1), PBD (pyrrolobenzodiazepine) dimer, and the like, but is not limited thereto.

In another embodiment of the present invention, the antibody-drug conjugate may be obtained according to a method well-known in the art.

In an aspect of the present invention, the antibody-drug conjugate may be characterized in that the antibody or antigen-binding fragment thereof is conjugated to the drug via a linker.

In another aspect of the present invention, the linker may be a cleavable linker or a non-cleavable linker.

The linker is a site for linking the antibody to the drug. For example, the linker allows the drug to be released in a cleavable form under an intracellular condition, that is, through cleavage of the linker from the antibody in an intracellular environment.

The linker may be a peptide linker that can be cleaved by a cleavage agent present in an intracellular environment, for example, in the lysosome or endosome, and can be cleaved by intracellular peptidases or proteases, such as lysosome or endosome proteases. Generally, a peptide linker is at least two amino acids in length. The cleavage agent may include cathepsin B, cathepsin D and plasmin, which hydrolyze the peptide to release the drug into the target cell. The peptide linker can be cleaved by a thiol-dependent protease cathepsin-B, which is highly expressed in cancer tissue. For example, the peptide linker may be a Phe-Leu or Gly-Phe-Leu-Gly linker. In addition, the peptide linker may, for example, be a Val-Cit linker or a Phe-Lys linker, which can be cleaved by an intracellular protease.

In an aspect of the present invention, the cleavable linker is sensitive to pH and may be sensitive to hydrolysis at a certain pH value. Generally, the pH-sensitive linker is a linker that can be hydrolyzed under acidic conditions. Examples of acid-instable linkers that can be hydrolyzed in lysosomes include hydrazone, semicarbazone, thiosemicarbazone, cis-aconitic amide, orthoester, acetal, ketal, and the like.

The linker may also be cleaved under reducing conditions, and may, for example, be a disulfide linker. A variety of disulfide bonds can be formed using N-succinimidyl-S-acetylthioacetate (SATA), N-succinimidyl-3-(2-pyridyldithio) propionate (SPDP), N-succinimidyl-3-(2-pyridyldithio)butyrate (SPDB) and N-succinimidyl-oxycarbonyl-alpha-methyl-alpha-(2-pyridyl-dithio)toluene (SMPT).

In an embodiment of the present invention, the drug and/or the drug-linker may be randomly conjugated through the lysine of the antibody, or may be conjugated through cysteine, which is exposed when the disulfide bond chain is reduced. In some cases, the linker-drug can be conjugated through cysteine present in a genetically engineered tag, e.g., a peptide or protein. The genetically engineered tag, e.g., a peptide or protein, may include an amino acid motif that can be recognized, for example, by an isoprenoid transferase. The peptide or protein has a deletion at the carboxyl terminus of the peptide or protein or an addition at the carboxyl (C) terminus of the peptide or protein through a covalent bond of a spacer unit. The peptide or protein may be covalently bonded directly to an amino acid motif, or may be linked to the amino acid motif through a covalent bond to the spacer unit. The amino acid spacer unit consists of 1 to 20 amino acids, and is particularly preferably a glycine unit.

The linker may comprise a beta-glucuronide linker that is recognized and hydrolyzed by beta-glucuronidase, which is present in multiple copies in the lysosome or overexpressed in some tumor cells. Unlike the peptide linker, this linker has the advantage of increasing the solubility of the antibody-drug conjugate when bound to a drug having high hydrophobicity due to the high hydrophilicity thereof.

In this regard, in embodiments of the present invention, it is possible to use a beta-glucuronide linker disclosed in Korean Patent Application Publication No. 2015-0137015, for example, a beta-glucuronide linker including a self-immolative group.

In addition, the linker may be, for example, a non-cleavable linker, and the drug may be released merely through a single step of hydrolyzing the antibody, thus producing, for example, an amino acid/linker/drug complex. This type of linker can be a thioether group or a maleimidocaproyl group, and is stable in the blood.

In an aspect of the present invention, the drug may be a chemotherapeutic agent, a toxin, microRNA (miRNA), siRNA, shRNA, or a radioactive isotope. The drug, which is an agent having a pharmacological effect, may be conjugated to the antibody.

The chemotherapeutic agent may be a cytotoxic agent or an immunosuppressive agent. Specifically, the chemotherapeutic agent may comprise a microtubulin inhibitor, a mitotic inhibitor, a topoisomerase inhibitor, or a chemotherapeutic agent capable of functioning as a DNA intercalator. The chemotherapeutic agent may also comprise an immunomodulatory compound, an anticancer agent, an antiviral agent, an antibacterial agent, an antifungal agent, an anthelmintic, or a combination thereof.

For example, the drug may comprise at least one selected from the group consisting of maytansinoid, auristatin, aminopterin, actinomycin, bleomycin, thalidomide, camptothecin, N8-acetylspermidine, 1-(2 chloroethyl)-1,2-dimethyl sulfonyl hydrazide, esperamycin, etoposide, 6-mercaptopurine, dolastatin, trichothecene, calicheamicin, taxol, taxane, paclitaxel, docetaxel, methotrexate, vincristine, vinblastine, doxorubicin, melphalan, chlorambucil, duocarmycin, L-asparaginase, mercaptopurine, thioguanine, hydroxyurea, cytarabine, cyclophosphamide, ifosfamide, nitrosourea, cisplatin, carboplatin, mitomycins (mitomycin A and mitomycin C), dacarbazine, procarbazine, topotecan, nitrogen mustard, cytoxan, etoposide, 5-fluorouracil, CNU (bis-chloroethylnitrosourea), irinotecan, camptothecin, bleomycin, idarubicin, daunorubicin, dactinomycin, plicamycin, asparaginase, vinorelbine, chlorambucil, melphalan, carmustine, lomustine, busulfan, treosulfan, dacarbazine, etoposide, teniposide, topotecan, 9-aminocamptothecin, crisnatol, trimetrexate, mycophenolic acid, tiazofurin, ribavirin, EICAR (5-ethynyl-1-beta-ribofuranosylimidazole-4-carboxamide), hydroxyurea, deferoxamine, floxuridine, doxifluridine, raltitrexed, cytarabine (ara C), cytosine arabinoside, fludarabine, tamoxifen, raloxifene, megestrol, goserelin, leuprolide acetate, flutamide, bicalutamide, EB1089, CB1093, KH1060, verteporfin, phthalocyanine, photosensitizer Pe4, demethoxy-hypocrellin A, interferon-α, interferon-γ, tumor necrosis factor, gemcitabine, Velcade, Revlimid, Thalomid, lovastatin, 1-methyl-4-phenylpyridiniumion, staurosporine, actinomycin D, dactinomycin, bleomycin A2, bleomycin B2, peplomycin, epirubicin, pirarubicin, zorubicin, mitoxantrone, verapamil and thapsigargin, nucleases, and toxins derived from bacteria or plants and animals, but the present invention is not limited thereto.

In an aspect of the present invention, the drug may have a nucleophile group selected from the group consisting of amine, thiol, hydroxyl, hydrazide, oxime, hydrazine, thiosemicarbazone, hydrazine carboxylate and aryl hydrazide groups, which can react with an electrophilic group on the linker and the linker reagent to form a covalent bond.

In still another aspect, the present invention is directed to a pharmaceutical composition for preventing and/or treating cancer, the pharmaceutical composition comprising the antibody or antigen-binding fragment thereof or the antibody-drug conjugate.

In yet another aspect, the present invention is directed to a method for treating cancer, the method comprising administering the antibody or antigen-binding fragment thereof or the antibody-drug conjugate to a patient in need of prevention or treatment.

In still yet another aspect, the present invention is directed to the use of the antibody or antigen-binding fragment thereof or the antibody-drug conjugate for treating cancer.

In further another aspect, the present invention is directed to the use of the antibody or antigen-binding fragment thereof or the antibody-drug conjugate in the manufacture of a medicament for treating cancer.

In an aspect of the present invention, the cancer may be ovarian cancer, breast cancer, lung cancer, kidney cancer, colon cancer, brain cancer, rectal cancer, cervical cancer, or endometrial cancer, but is not limited thereto.

Although the pharmaceutical composition comprising the antibody or antigen-binding fragment thereof or the antibody-drug conjugate according to embodiments of the present invention may also comprise only the antibody or antigen-binding fragment thereof or the antibody-drug conjugate as an active ingredient, it is generally mixed with one or more pharmacologically acceptable carriers, and is preferably provided as a pharmaceutical formulation prepared by any method known in the technical field of pharmaceuticals.

The pharmaceutical composition of embodiments of the present invention may be used alone or in combination with at least one therapeutic drug selected from the above-described radioisotopes, low-molecular-weight drugs, polymer drugs or antibody drugs. In addition, the pharmaceutical composition of embodiments of the present invention may be used in combination with a conventional therapeutic agent. That is, the pharmaceutical composition comprising the antibody or antigen-binding fragment thereof or the antibody-drug conjugate according to an embodiment the present invention may be administered simultaneously or sequentially with a conventional therapeutic agent such as an anticancer agent.

As the route of administration, it is preferable to use the most effective route of administration at the time of treatment. Examples of the route of administration include oral administration or parenteral administration such as intra-mouth, intra-airway, intrarectal, subcutaneous, intramuscular or intravenous administration. Intravenous administration is preferred.

Dosage forms include a spray, a capsule, a tablet, a powder, a granule, a syrup, an emulsion, a suppository, an injection, an ointment, or a tape.

The dosage or the frequency of administration varies according to the desired therapeutic effect, the mode of administration, the period of treatment, and the patient's age and body weight, but is usually 10 μg/kg to 10 mg/kg per day for an adult.

Since the antibody or antigen-binding fragment thereof according to the present invention binds specifically to folate receptor-α (FOLR1), FOLR1 may be detected or diagnosed using the same. Expression of FOLR1 is related to several diseases, for example, cancer.

Therefore, in another aspect, the present disclosure is directed to a composition for diagnosing disease, the composition comprising the antibody or antigen-binding fragment thereof.

In an aspect of the present invention, the disease may be FOLR1-related disease, for example, cancer, but is not limited thereto.

In still another aspect, the present invention is directed to a method for diagnosing disease or a method for providing information for diagnosing disease, the method comprising a step of treating (administering) a biological sample isolated from a subject with the antibody or antigen-binding fragment thereof.

In another aspect of the present invention, the method for diagnosing disease may further comprise, after the treatment step, a step of identifying whether an antigen-antibody reaction occurs. In the detection method, when the antigen-antibody reaction is detected, a FOLR1-related disease, for example, cancer, may be determined to be present in the biological sample or a patient from which the biological sample has been obtained. Thus, the method may further comprise, after the step of identifying, a step of determining that, when the antigen-antibody reaction is detected, the biological sample or the patient is a FOLR1-related disease patient, for example, a cancer patient. The biological sample may be selected from the group consisting of cells, tissues, body fluids, cultures thereof and the like, obtained (isolated) from a mammal such as a human (e.g., a cancer patient).

The step of identifying whether or not the antigen-antibody reaction occurs may be performed through various methods known in the art. For example, the step may be performed through a conventional enzymatic reaction, fluorescence, luminescence and/or radiation detection. Specifically, the step may be performed by a method selected from the group consisting of immunochromatography, immunohistochemistry, enzyme-linked immunosorbent assay (ELISA), radioimmunoassay (RIA), enzyme immunoassay (EIA), fluorescence immunoassay (FIA), luminescence immunoassay (LIA), Western blotting, microarray, and immunoprecipitation assay, but is not limited thereto.

In this case, the antibody or antigen-binding fragment thereof may further comprise a marker. The marker may be at least one selected from the group consisting of radioactive isotopes, fluorescent substances, chromogen and dyeing substances. The marker may be bound (linked) to the antibody or antigen-binding fragment by a conventional method (for example, a chemical bond such as a covalent bond, coordination bond or ionic bond). The binding of the antibody (or antigen-binding fragment) to the marker may be performed in accordance with techniques known in the art.

Hereinafter, various embodiments of the present invention will be described in more detail with reference to examples. It will be obvious to those skilled in the art that these examples are merely to illustrate the present invention, and the scope of the present invention is not limited by these examples.

Example 1: Selection of Library Clones

To obtain optimum sequences having improved binding affinity for FOLR1, CDR libraries were constructed using Fab fragments.

Example 1-1: Preparation of Parent Antibody Fab Template

Variable regions were synthesized from the light chain and heavy chain of a parent antibody, respectively, and constant regions were synthesized from pComb3X-TT. PCR reaction was performed under the following conditions: pre-denaturation at 94° C. for 2 min, and then 25 cycles, each consisting of 30 sec at 94° C., 30 sec at 56° C. and 30 sec at 72° C., followed by elongation at 72° C. for 7 min. In the PCR reaction, 100 ng of one template was used, or a mixture obtained by mixing two templates in an amount of 3 µL of each template was used. 3 µL of each primer was used at a concentration of 20 pM, 0.05 mM dNTP and 0.5 µL (2.6 units) Taq polymerase were used, and the reaction volume was 100 µL. After completion of the reaction, whether amplification occurred was checked using 1% agarose gel electrophoresis, and the amplification product was purified using a QIAGEN' gel extraction kit. For second and third PCR, overlapping PCR was performed using the amplified fragment as a template. The PCR reaction product DNA was purified on an agarose gel using a Qiagen gel extraction kit, cleaved with a SfiI restriction enzyme, and then subjected to gel extraction. 153 ng of the SfiI-cleaved antibody gene and 136 ng of the SfiI-cleaved pComb3X vector were mixed with each other, added to 10× T4 DNA ligation buffer and 10 units of ligase, reacted at room temperature for 3 hours, and then heat-shocked at 42° C. for 45 seconds in E. coli DH5a cells, followed by incubation at 37° C. for 1.5 hours. From the colony obtained by the above-described transformation method, a template for antibody library construction composed of a 50-kDa Fab fragment was obtained.

Example 1-2: Antibody Library Construction

Libraries were constructed by artificially introducing diversity into the complementarity-determining region, and the CDRs and FRs of a given antibody can be identified according to the procedure of UCL, Antibody Informatics (www.bioinf.org.uk/abs/).

Libraries were constructed by randomizing the CDR sequences of the parent antibody based on the template prepared in Example 1-1. Among the six CDRs of the parent antibody, CDR-H2 was excluded from the experiment because it was so long as to be difficult to handle in the experiment. The CDR sequence of the parent antibody is shown in Table 1 below.

TABLE 1

| CDR sequence of parent antibody | | | |
|---|---|---|---|
| CDR | Residue located in front | Sequence | Residue located at back |
| CDR-H1 | Cys-Xaa-Xaa-Xaa (SEQ ID NO: 51) | GFTFSGYGLS (SEQ ID NO: 3) | Trp-Val |
| CDR-H2 | Leu-Gln-Trp-Val-Ala (SEQ ID NO: 52) | MISSGGSYTYYADSV (SEQ ID NO: 4) | Lys |
| CDR-H3 | Cys-Ala-Arg | HGDDPAWFAY (SEQ ID NO: 5) | Trp-Gly-Gln-Gly (SEQ ID NO: 9) |
| CDR-L1 | Cys | SVSSSISSNNLH (SEQ ID NO: 6) | Trp |
| CDR-L2 | Ile-Tyr | GTSNLAS (SEQ ID NO: 7) | Gly |
| CDR-L3 | Cys | QQWSSYPYMYT (SEQ ID NO: 8) | Phe-Gly-Gln-Gly (SEQ ID NO: 54) |

To randomize a specific position in the region that binds to an antigen, primers were prepared using mixed base codes (Table 2). The mixed base code is a degenerated primer and refers to an oligonucleotide in which two or more bases exist in one position so that they can bind to similar nucleotide sequences in consideration of the nucleotide sequence similarity. Prior to preparation of the primers, in order to determine the specific position to be randomized, conserved residues were identified through CDR sequence analysis of the parent antibody. For codon diversification of a portion excluding these residues, primers were prepared using mixed base codes.

TABLE 2

Primer sequences

| CDR | Primer | Sequence (5' → 3') | SEQ ID NO: |
|---|---|---|---|
| CDR-H1 | Far1-H1-random-f | GCC TCT GGC TTC ACT TTC AGT RRT TAC GVT MTG ART TGG GTG AGA CAG GCA CCT G | 9 |
| | Fan1-H1-b | ACT GAA AGT GAA GCC AGA GGC | 10 |
| CDR-H3 | Far1-H3-random1-f | GGG GTC TAT TTT TGT GCA AGA NNK NNK GAC GAT CCA GCA TGG TTT GMT TAC TGG GGC CAA GGG ACC | 11 |
| | Far1-H3-random2-f | GGG GTC TAT TTT TGT GCA AGA CAC NNK NNK GAT CCA GCA TGG TTT GMT TAC TGG GGC CAA GGG ACC | 12 |
| | Far1-H3-random3-f | GGG GTC TAT TTT TGT GCA AGA CAC GGT NNK NNK CCA GCA TGG TTT GMT TAC TGG GGC CAA GGG ACC | 13 |
| | Far1-H3-random4-f | GGG GTC TAT TTT TGT GCA AGA CAC GGT GAC NNK NNK GCA TGG TTT GMT TAC TGG GGC CAA GGG ACC | 14 |
| | Far1-H3-random5-f | GGG GTC TAT TTT TGT GCA AGA CAC GGT GAC GAT NNK NNK TGG TTT GMT TAC TGG GGC CAA GGG ACC | 15 |
| | Far1-H3-random6-f | GGG GTC TAT TTT TGT GCA AGA CAC GGT GAC GAT CCA NNK NNK TTT GMT TAC TGG GGC CAA GGG ACC | 16 |
| | Far1-H3-b | TCT TGC ACA AAA ATA GAC CCC | 17 |
| CDR-L1 | Far1-L1-random-f | AC AGA GTC ACC ATC ACA TGC AGK GYT TCC TCC RGT VTT AGT TCA ARC WAT CTG MAC TGG TAT CAG CAG AAG CCC G | 18 |
| | Far1-L1-b | GCA TGT GAT GGT GAC TCT GT | 19 |
| CDR-L2 | Far1-L2-random-f | C CCA AAG CCC TGG ATC TAC GVT RCC TCT AVT CKG GMA AST GGG GTG CCT TCA AGG TTC A | 20 |
| | Far1-L2-b | GTA GAT CCA GGG CTT TGG G | 21 |
| CDR-L3 | Far1-L3-random-f | GCA ACT TAC TAT TGC CAG CAG NNK BMT WAT TWT CCA YMT NNK YMC ACC TTC GGT CAG GGC AC | 22 |
| | Far1-L3-b | CTG CTG GCA ATA GTA AGT TGC | 23 |
| All CDRs | pC3X-f | GCA CGA CAG GTT TCC CGAC | 24 |
| | pC3X-b | AAC CAT CGA TAG CAG CAC CG | 25 |
| CDR-L3H3 | Lead-b | GGC CAT GGC TGG TTG GGC | 26 |
| | Lead-VH | GCC CAA CCA GCC ATG GCC | 27 |

For codon randomization of the parent antibody CDR-L1, L2, L3, H1 and H2 regions, each of the regions was amplified by PCR and attached to PCR-amplified CDR DNA through overlap extension PCR, thereby constructing single-CDR libraries having diversity only in one CDR and multiple-CDR libraries having diversity in two CDRs. The PCR reaction was performed under the following conditions: pre-denaturation at 94° C. for 2 min and then 25 cycles, each consisting of 30 sec at 94° C., 30 sec at 56° C. and 30 sec at 72° C., followed by extension at 72° C. for 7 min. However, the elongation time at 72° C. was adjusted to 1 min 30 sec or 2 min depending on the length of predicted DNA fragment products. Specifically, the elongation time was 1 min 30 sec for a predicted length of 500 to 1,500 bp and 2 min for a predicted length of 1,500 to 2,000 bp. The names of the templates, primers and products used in these processes are summarized in Table 3 below. The constructed single- or multiple-CDR library was isolated and purified by 1% agarose gel electrophoresis, and the purification product was cleaved by treatment with a SfiI restriction enzyme at 50° C. for 12 hours or more. The pComb3X phagemid vector was also cleaved with a SfiI restriction enzyme in the same manner.

TABLE 3

PCR templates and primers for library construction

| PCR | | Template | Primer SEQ ID NOS: | Product |
|---|---|---|---|---|
| Single-CDR library | | | | |
| CDR-L1 | $1^{st}$ | pFAR-FabC3 | 19, 24 | FAR-L1-F |
| | | | 18, 25 | FAR-L1-R |
| | $2^{nd}$ | FAR-L1-F, FAR-L1-R | 24, 25 | FAR-CDR-L1 |
| CDR-L2 | $1^{st}$ | pFAR-FabC3 | 21, 24 | FAR-L2-F |
| | | | 20, 24 | FAR-L2-R |
| | $2^{nd}$ | FAR-L2-F, FAR-L2-R | 24, 25 | FAR-CDR-L2 |
| CDR-L3 | $1^{st}$ | pFAR-FabC3 | 23, 24 | FAR-L3-F |
| | | | 22, 25 | FAR-L3-R |
| | $2^{nd}$ | FAR-L3-F, FAR-L3-R | 24, 25 | FAR-CDR-L3 |
| CDR-H1 | $1^{st}$ | pFAR-FabC3 | 10, 24 | FAR-H1-F |
| | | | 9, 25 | FAR-H1-R |
| | $2^{nd}$ | FAR-H1-F, FAR-H1-R | 24, 25 | FAR-CDR-H1 |
| CDR-H3 | $1^{st}$ | pFAR-FabC3 | 17, 24 | FAR-H3-F |
| | | | 11 to 16, 25 | FAR-H3-R |
| | $2^{nd}$ | FAR-H3-F, FAR-H3-R | 24, 25 | FAR-CDR-H3 |
| Multiple-CDR library | | | | |
| CDR-L3H3 | $1^{st}$ | pFAR CDR-L3 | 24, 26 | FAR-L3 |
| | | pFAR-CDR-H3 | 25, 27 | FAR-H3 |
| | $2^{nd}$ | FAR-L3, FAR-H3 | 24, 25 | FAR-CDR-L3H3 |

For ligation, the SfiI-cleaved vector and the SfiI-cleaved insert were mixed together in equal amounts and reacted overnight at room temperature. If the volume of the ligation product is too large for transformation, the volume of the ligation product can be reduced using EtOH precipitation, and the method for reducing the volume is as follows. To 50 µL of the ligation product, 5 µL (1/10) of 3 M sodium acetate (pH 5.2) and 110 µL (2-fold) of 100% EtOH were added, and DNA was allowed to precipitate at −20° C. for 2 hours or more. The precipitated DNA was centrifuged at 12,000 rpm for 15 minutes, and then washed with 1 ml of 70% EtOH and centrifuged under the same conditions. The pellet was dried, and then dissolved in 10 µL of deionized water. Transformation was performed by electroporation. Specifically, 10 µL of the ligation product and 50 µL of *E. coli* TG1 competent cells were mixed together and then placed in a 0.2-cm cooled cuvette, which was placed in an electroporator. Next, the cells were pulsed at 2.5 kV for 4 to 5 msec. 2 mL of recovery medium heated to 37° C. was added thereto, immediately after pulsing and then incubation was performed at 37° C. for 1 hour. Next, 1 µL of the incubated cells was diluted 1,000-fold with SB medium, and 10 µL and 100 µL of the cell dilution were dispensed on an LB agar plate to prepare samples for measuring the library size, and the remainder was plated on one plate and incubated overnight at 37° C. The next day, the library size was measured by counting the number of colonies on the plate into which the diluted cells were dispensed. In addition, 5 mL of SB medium was added to the plate into which the undiluted cells were dispensed, the cells were collected using a spreader, and then a 0.5-fold volume of 50% glycerol was added to the cells, which were then stored in a deep freezer (−75° C.)

TABLE 4

| CDR library | Library size |
|---|---|
| CDR-L1 | $4.56 \times 10^6$ |
| CDR-L2 | $2.94 \times 10^7$ |
| CDR-L3 | $6.22 \times 10^7$ |
| CDR-H1 | $4.78 \times 10^6$ |
| CDR-H3 | $1.30 \times 10^8$ |
| CDR-L3H3 | $8.82 \times 10^7$ |

The size of the obtained library indicates transformation efficiency, specifically the number of individual clones. As a result, it can be considered that antigen-binding diversity corresponds to the library size. That is, the following libraries were prepared: a CDR-L1 library having a diversity of $10^6$, a CDR-L2 library having a diversity of $10^7$, a CDR-L3 library having a diversity of $10^7$, a CDR-H1 library having a diversity of $10^6$, a CDR-H3 library having a diversity of $10^8$, and a CDR-L3H3 library having a diversity of $10^7$ (Table 4).

Example 1-3: Selection by ELISA after Phage-Display Panning

Panning was performed to select a library clone that binds to human FOLR1, and as panning was repeated, a clone having further increased binding affinity for FOLR1 could be obtained.

For library amplification and recovery of a Fab-expressing bacteriophage, 100 µL of a TG1 stock transformed with the library was seeded into 20 mL of SB/Amp+2% glucose medium, and the library was expressed in *E. coli* TG1 cells at 37° C. and 220 rpm for 1.5 to 2 hours. The cell culture was centrifuged at 3500 rpm for 15 minutes. The supernatant was removed, and the pellet was re-suspended in 20 ml of SB/Amp medium. 0.5 mL of helper phage VCSM13 (about 1011 pfu) was added to the suspension, which was then infected with the helper phage by culture at 37° C. at 120 rpm for 1 hour. Next, kanamycin (50 mg/mL) was added to the suspension to reach 70 μg/mL, followed by culture at 30° C. at 200 rpm for 16 hours. The culture was centrifuged, and 5 mL of 5×PEG concentrated solution was added to the phage-containing supernatant, which was then concentrated on ice for 30 minutes. The concentrate was centrifuged at 12,000 rpm for 15 minutes, and the supernatant was removed. The phage pellet was re-suspended in 0.3 mL of PBS to obtain a library phage (for storage, a 0.5-fold volume of 50% glycerol is added to the library phage which is then stored at −75° C.)

To amplify the obtained library phage, an *E. coli* TG1 cell stock was seeded into 10 mL of SB medium, and cultured in an incubator at 37° C. at 220 rpm for about 4 to 5 hours up to the mid-log phase ($OD_{600}$=0.5 to 1.0), thus preparing competent cells which were then stored at 4° C. until use. Panning was performed in the following manner. 1 μg/mL of FOLR1 was coated on an immunotube, and then blocked with a blocking solution (3% skim milk) at 37° C. for 1 hour. 0.5 mL of the library phage was blocked by adding 0.5 mL of blocking solution thereto at a ratio of 1:1, and then allowed to react with the immobilized antigen. After the reaction had proceeded for one hour or more, unreacted or weakly bound phage was removed through a washing step with PBS-Tween20 buffer, and strongly bound phage was eluted out with 1 mL of TEA (100 mM) for 10 minutes and then neutralized with 0.5 mL of Tris-HCl (1 M, pH 7.4). 1.5 mL of the eluted phage was added to 8.5 mL of the competent cells and infected into the cells in an incubator at 37° C. at 120 rpm for 1 hour. Next, to measure the library size, 1 μL of the 2 mL reaction solution was diluted 1,000-fold and 10,000-fold and plated, and the remaining reaction solution was plated on one plate and incubated overnight at 37° C.

The transformed *E. coli* library was cultured and infected with VCSM13 helper phage to obtain an antibody phage library having Fab clones displayed on the surface thereof. Only phage clones that bound strongly to FOLR1 were selected by panning the library for 3 to 5 rounds against FOLR1 adsorbed on the immune-tube surface. Through this process, clones that bound weakly to FOLR1 or did not bind to FOLR1 due to defects in the synthesized CDR sequence were removed, and as a result, it was possible to select CDR sequences that had no defects and were better optimized than the existing sequences. The CDR-L1 and CDR-L2 libraries were panned for 5 rounds, the CDR-L3, CDR-H3 and CDR-L3H3 libraries were panned for 4 rounds, and the CDR-H1 library was panned for 3 rounds. For each panning round, the ratio (0/I ratio) of the eluted phage (output phage) to the phage (input phage) used in panning was calculated, and the results were expressed as % bound in Table 5 below. The fact that similar % bound values appear even when panning is repeated indicates that the binding affinity for FOLR1 reached saturation (Table 5). When this result appeared, panning was no longer performed, and the next step was performed using the eluted phage. To validate the functionality of the antibody phage libraries that resulted from panning, 94 clones were screened from each CDR library by ELISA. The number of ELISA-positive clones showing a binding signal at least 3 times stronger than the background signal was identified to be 92 for CDR-L1, 66 for CDR-L2, 19 for CDR-L3, 94 for CDR-H1, 48 for CDR-H3, and 63 for CDR-L3H3. Eight clones among the clones showing a stronger binding signal for each library were sequenced (Table 6).

TABLE 5

Panning conditions and results

| Phage library | Panning round | Phage input (c.f.u) | Phage output (c.f.u) | % Bound | Number of washings | Amount of antigen |
|---|---|---|---|---|---|---|
| CDR-L1 | 1 | $3.6 \times 10^{10}$ | $5.1 \times 10^8$ | 1.4 | 3 | 1.0 μg |
| | 2 | $\sim 10^{10}$ | $8.5 \times 10^8$ | 8.5 | 5 | 0.5 μg |
| | 3 | $\sim 10^{10}$ | $1.1 \times 10^9$ | 11 | 10 | 0.1 μg |
| | 4 | $\sim 10^{10}$ | $5.9 \times 10^8$ | 5.9 | 10 | 0.1 μg |
| | 5 | $\sim 10^{10}$ | $4.3 \times 10^8$ | 4.3 | 10 | 0.1 μg |
| CDR-L2 | 1 | $2.5 \times 10^{10}$ | $6.8 \times 10^8$ | 2.7 | 3 | 1.0 μg |
| | 2 | $\sim 10^{10}$ | $7.5 \times 10^8$ | 7.5 | 5 | 0.5 μg |
| | 3 | $\sim 10^{10}$ | $8.0 \times 10^8$ | 8.0 | 10 | 0.1 μg |
| | 4 | $\sim 10^{10}$ | $3.2 \times 10^8$ | 3.2 | 10 | 0.1 μg |
| | 5 | $\sim 10^{10}$ | $3.1 \times 10^8$ | 3.1 | 10 | 0.1 μg |
| CDR-L3 | 1 | $1.4 \times 10^9$ | $4.3 \times 10^6$ | 0.3 | 3 | 1.0 μg |
| | 2 | $3.7 \times 10^8$ | $1.0 \times 10^5$ | $2.7 \times 10^{-2}$ | 5 | 0.5 μg |
| | 3 | $1.7 \times 10^9$ | $7.2 \times 10^7$ | 4.2 | 5 | 0.5 μg |
| | 4 | $5.8 \times 10^9$ | $8.0 \times 10^7$ | 1.4 | 10 | 0.1 μg |
| CDR-H1 | 1 | $5.5 \times 10^{10}$ | $4.9 \times 10^8$ | 0.9 | 3 | 1.0 μg |
| | 2 | $\sim 10^{10}$ | $6.2 \times 10^8$ | 6.2 | 5 | 0.5 μg |
| | 3 | $\sim 10^{10}$ | $6.5 \times 10^8$ | 6.5 | 10 | 0.1 μg |
| CDR-H3 | 1 | $1.9 \times 10^9$ | $2.2 \times 10^7$ | 1.2 | 3 | 1.0 μg |
| | 2 | $3.5 \times 10^8$ | $1.0 \times 10^5$ | $2.9 \times 10^{-2}$ | 5 | 0.5 μg |
| | 3 | $1.8 \times 10^9$ | $8.6 \times 10^7$ | 4.8 | 5 | 0.5 μg |
| | 4 | $4.4 \times 10^9$ | $1.1 \times 10^8$ | 2.5 | 10 | 0.1 μg |
| CDR-L3H3 | 1 | $8.9 \times 10^8$ | $1.0 \times 10^8$ | 11.2 | 3 | 1.0 μg |
| | 2 | $6.0 \times 10^8$ | $1.0 \times 10^5$ | $1.7 \times 10^{-2}$ | 5 | 0.5 μg |
| | 3 | $1.8 \times 10^9$ | $2.6 \times 10^7$ | 1.4 | 5 | 0.5 μg |
| | 4 | $3.2 \times 10^9$ | $4.0 \times 10^7$ | 1.3 | 10 | 0.1 μg |

TABLE 6

Sequencing results

| CDR | Clone | Sequencing results (SEQ ID NO:) |
|---|---|---|
| CDR-L1 | WT | SVSSSISSNNLH (SEQ ID NO: 6) |
| | C6, E6 | SASSGLSSSYLH (SEQ ID NO: 29) |
| | C7 | SASSSLSSSYLH (SEQ ID NO: 35) |
| | D5 | RVSSGISSNNLH (SEQ ID NO: 36) |
| | D7 | RASSGLSSNNLH (SEQ ID NO: 37) |
| | F3 | RASSGVSSNNLH (SEQ ID NO: 38) |
| | H1 | SASSSISSSYLH (SEQ ID NO: 39) |
| | H7 | SVSSSLSSSNLH (SEQ ID NO: 40) |
| CDR-L2 | WT | GTSNLAS (SEQ ID NO: 7) |
| | B1 | ATSSRAT (SEQ ID NO: 41) |
| | C1 | GTSSRAS (SEQ ID NO: 30) |
| | C3 | ATSNRES (SEQ ID NO: 42) |
| | C10 | ATSSLAT (SEQ ID NO: 43) |
| | E9, G6 | GASSLAT (SEQ ID NO: 44) |
| | G3 | ATSNLAS (SEQ ID NO: 45) |
| | H2 | TASSRAS (SEQ ID NO: 46) |
| CDR-H3 | WT | HGDDPAW (SEQ ID NO: 47) |
| | B4, B8, C4, C6, C10, G5 | HGDDVAW (SEQ ID NO: 48) |
| | C8 | HGDDIAW (SEQ ID NO: 49) |
| CDR-L3H3 | WT | HGDDPAW (SEQ ID NO: 47) |
| | A3, A8, A10, F8, H4, H6, H10 | HGDDVAW (SEQ ID NO: 48) |
| | G8 | HGDDISW (SEQ ID NO: 50) |

Example 1-4: Fab Production Using Protein-Expressing Strain TOP10F' and Purification To compare the binding affinities of the selected clones for FOLR1, purification of each clone was performed. Prior to purification, the host strain was changed from TG1 to TOP10F' cells to express only a Fab region.

A colony corresponding to each of the selected clones was seeded into 4 mL SB/ampicillin medium and cultured overnight at 37° C. The next day, 4 ml of the overnight culture was seeded into 400 mL SB/ampicillin medium and cultured in an incubator at 37° C. for about 3 to 4 hours until the $OD_{600}$ reached 0.5 to 1.0. Next, for expression of the clone, the culture was treated with IPTG to a final concentration of 1 mM and then cultured overnight at 30° C. However, when only expression was to be confirmed, culture was performed in 20 mL of SB/ampicillin medium.

To recover a periplasm from 400 mL of the culture, the culture was centrifuged to remove the supernatant, and then the cells were lysed by treatment with 16 mL of 1×TES solution at 4° C. and incubation at 4° C. for 1 hour. Additionally, the cells were treated with 24 mL of 0.2×TES solution and incubated for 1 hour. Next, the supernatant was collected by centrifugation and 5 mM $MgCl_2$ was added thereto in order to remove EDTA. Before loading of the sample, a column packed with 0.5 mL of Ni-NTA His-Bind® resin was washed with 20 CV of elution buffer (300 mM imidazole in PBS, pH 7.4) and then flushed with 20 CV of PBS. The sample was loaded onto the column and the flow-through was collected. After completion of loading, the column was flushed with 20 CV of wash buffer (20 mM imidazole in PBS, pH 7.4) and the washing-through was collected. Then, the column was flushed with 10 CV of elution buffer and the eluent was collected. 15 μL of the sample collected in each step during the purification process was loaded in each well in 12% SDS-PAGE and electrophoresed (at 150 V for 1 hour). The band was visualized by Coomassie blue staining.

Example 1-5: Examination of Direct Binding Pattern of Selected Clone to FOLR1 at Different Concentrations For the purpose of comparing the binding affinities of the primarily selected clones with each other, ELISA was performed at different clone concentrations in the following manner. 25 μL of FOLR1 was added to each well of a 96-well plate at a concentration of 1 μg/mL, coated on the plate at room temperature for 1 hour, and then blocked with 180 μL of 3% skim milk at room temperature for 1 hour. During blocking, samples to be used as primary antibodies were prepared. As primary antibodies, samples selected by screening were used. The samples were diluted to a concentration of 0.1 to 100 nM (0, 0.1, 0.3, 1, 3, 10, 30, and 100 nM) and cold-stored until use. After blocking, 3% skim milk was removed, and 25 μL of the primary antibody was added to each well and allowed to react at room temperature for 1 hour or more. After completion of the reaction, each well was washed three times with PBS-Tween20 (0.1%) buffer. As a secondary antibody, HA-HRP was diluted 3,000-fold with 3% skim milk, and 25 μL of the dilution was added to each well and allowed to react at room temperature for 1 hour or more. After completion of the reaction, each well was washed three times with PBS-Tween20 (0.1%), and 25 μL of substrate TMB was added to each well to confirm color development. After about 5 minutes, 25 μL of 1 M $H_2SO_4$ was added to each well to stop the reaction, and the absorbance at a wavelength of 450 nm was measured. From the measurement results, the EC (Effector concentration) value was calculated using the GraphPad Prism 7 program.

To measure the binding affinity of the selected clone for FOLR1, SPR measurement was performed using a Biacore3000. Before each sample was loaded, a CM5 sensor chip was activated with 0.1 M NHS/0.4 M EDC, and then FOLR1 (20 μg/mL in 10 mM acetate, pH 5.0) was immobilized thereon. Then, unreacted NHS was deactivated with 1 M ethanolamine. 250 μL of each sample was prepared at concentrations of 1, 2, 5, 10, 20 and 40 nM, and association and dissociation sensorgrams were obtained while each sample was flushed at 30 μl/min. The sensor chip was regenerated with 10 mM glycine (pH 2.1). The obtained sensorgrams were analyzed using the BIAevaluation software, and the KD values were calculated.

Example 1-6: Sequencing of Antibody Library

The sequences of the randomized complementarity-determining regions of the clones selected by ELISA of the phage library were analyzed. Using, as a template, 1 μL of a culture of each clone selected from the clones cultured in the 96-well plate, PCR reaction was performed using pC3X-f and pC3X-b primers under the following conditions: pre-denaturation at 94° C. for 2 minutes, and then 25 cycles, each consisting of 30 sec at 94° C., 30 sec at 56° C. and 2 min at 72° C., followed by elongation at 72° C. for 7 min. Whether amplification occurred was checked by 1% agarose gel electrophoresis, and the amplified PCR product was purified with DW using a QIAvac 96 and sequenced. The sequence of the complementarity-determining region was analyzed using the leader sequence.

Example 2: Construction of Modified Antibody (vAb)

The final clone pvAb was constructed in the same manner as the antibody library construction method. The templates and primers used are shown in Table 7 below, and information about the vAb antibody sequence is summarized in Tables 8 to 10 below.

TABLE 7

PCR templates and primers for final clone construction

| Clone | PCR | Template | Primer | Product |
|---|---|---|---|---|
| pvAb | 1st | pCDR-L1#C6 | pC3X-f, Farl-L2-b | CDR-L1 |
|  |  | pCDR-L2#C1 | Farl-L2-f, Lead-b | CDR-L2 |
|  |  | CDR-L3H3#A3 | Lead-VH, pC3X-b | CDR-H3 |
|  | 2nd | CDR-L2, CDR-H3 | Farl-L2-f, pC3X-b | CDR-L2H3 |
|  | 3rd | CDR-L1, CDR-L2H3 | pC3X-f, pC3X-b | CDR-L1L2H3 |

TABLE 8

Sequence comparison of complementarity-determining region between parent antibody and modified antibody (vAb)

| CDR region | Parent antibody CDR sequence | Position in sequence | Amino acid of parent antibody | Amino acid after modification | CDR sequence of modified antibody |
|---|---|---|---|---|---|
| CDR-H3 | HGDDPAWFAY (SEQ ID NO: 5) | 103 | P | V | HGDDVAWFAY (SEQ ID NO: 28) |
| CDR-L1 | SVSSSISSNNLH (SEQ ID NO: 6) | 25 | V | A | SASSGLSSSYLH (SEQ ID NO: 29) |
|  |  | 28 | S | G |  |
|  |  | 29 | I | L |  |
|  |  | 32 | N | S |  |
|  |  | 33 | N | Y |  |
| CDR-L2 | GTSNLAS (SEQ ID NO: 7) | 54 | N | S | GTSSRAS (SEQ ID NO: 30) |
|  |  | 55 | L | R |  |

Through combinations of the CDR sequences identified as described above, the modified antibodies vAb1, vAb2, vAb3, vAb4 and vAb5 were constructed. vAb1 is a modified antibody that reflects all of CDR-H3, CDR-L1 and CDR-L2, vAb2 is a modified antibody that reflects CDR-L1 and CDR-L2, vAb3 is a modified antibody that reflects CDR-L1, vAb4 is a modified antibody that reflects CDR-L2, and vAb5 is a modified antibody that reflects CDR-H3.

TABLE 10

Sequences of modified antibodies (vAb)

| Modified antibody | HC | LC |
|---|---|---|
| vAb1 | SEQ ID NO: 31 | SEQ ID NO: 32 |
| vAb2 | SEQ ID NO: 1 | SEQ ID NO: 32 |

TABLE 9

Amino acid sequences of parent antibody and modified antibody (vAb)

| Type | Sequence | SEQ ID NO |
|---|---|---|
| HC | EVQLVESGGGVVQPGRSLRLSCSASGFTFSGYGLSWVRQAPGKGLEWVAMISSGGSYTYYADSVKGRFAISRDNAKNTLFLQMDSLRPEDTGVYFCARHGDDPAWFAYWGQGTPVTVSS | 1 |
| LC | DIQLTQSPSSLSASVGDRVTITCSVSSSISSNNLHWYQQKPGKAPKPWIYGTSNLASGVPSRFSGSGSGTDYTFTISSLQPEDIATYYCQQWSSYPYMYTFGQGTKVEIK | 2 |
| HC | EVQLVESGGGVVQPGRSLRLSCSASGFTFSGYGLSWVRQAPGKGLEWVAMISSGGSYTYYADSVKGRFAISRDNAKNTLFLQMDSLRPEDTGVYFCARHGDDVAWFAYWGQGTPVTVSS | 31 |
| LC | DIQLTQSPSSLSASVGDRVTITCSASSGLSSSYLHWYQQKPGKAPKPWIYGTSSRASGVPSRFSGSGSGTDYTFTISSLQPEDIATYYCQQWSSYPYMYTFGQGTKVEIK | 32 |
| LC | DIQLTQSPSSLSASVGDRVTITCSASSGLSSSYLHWYQQKPGKAPKPWIYGTSNLASGVPSRFSGSGSGTDYTFTISSLQPEDIATYYCQQWSSYPYMYTFGQGTKVEIK | 33 |
| LC | DIQLTQSPSSLSASVGDRVTITCSVSSSISSNNLHWYQQKPGKAPKPWIYGTSSRASGVPSRFSGSGSGTDYTFTISSLQPEDIATYYCQQWSSYPYMYTFGQGTKVEIK | 34 |

TABLE 10-continued

Sequences of modified antibodies (vAb)

| Modified antibody | HC | LC |
|---|---|---|
| vAb3 | SEQ ID NO: 1 | SEQ ID NO: 33 |
| vAb4 | SEQ ID NO: 1 | SEQ ID NO: 34 |
| vAb5 | SEQ ID NO: 31 | SEQ ID NO: 2 |

Example 3: Expression and Purification of Modified Antibody (vAb)

To produce the modified antibody (vAb), expiCHO cells were transfected with a vector (pc 3.4-vAbL, pc 3.4-vAbH) containing the gene encoding the modified antibody (vAb) protein and cultured, and the modified antibody was purified using affinity chromatography. An XK16 column packed with the affinity resin MabSelect SuRe™ (GE Healthcare) was equilibrated by flushing with buffer A (25 mM Tris, pH 7.0, 25 mM NaCl), and then the culture was flushed and bound to the affinity resin, and the modified antibody (vAb) protein was eluted with buffer B (25 mM citric acid, pH 3.5). After completion of purification, the column was washed with 0.5 M NaOH, and then packed with 20% ethanol and cold-stored. The pH of the eluted sample was adjusted to 6.0 by adding a suitable amount of 1 M Tris (pH 9.0) thereto.

The state of the sample was checked through 10% SDS-PAGE. The obtained modified antibody (vAb) protein was subjected to buffer exchange by dialysis against a buffer containing 10 mM sodium succinate and 30 mM sucrose (pH 6.0).

Example 4: Analysis of Binding Affinity of Modified Antibody (vAb) by ELISA Assay For the purpose of comparing the binding affinity of the modified antibody (vAb) produced in Example 2 with that of the parent antibody, ELISA was performed at an antibody concentration of 0.006 to 6.250 ng/mL in the same manner as described in Examples 1-5. As a result of the measurement, it was confirmed that the modified antibodies vAb1 to vAb5 bound to FOLR1 with a 4.48- to 1.42-fold higher binding affinity than the parent antibody (Table 11). The measured values are obtained in different experiments for comparison with the parent antibody.

TABLE 11

Results of ELISA assay

| Coating | Sample | EC50 ng/mL | Relative Potency | $R^2$ |
|---|---|---|---|---|
| FOLR1-Fc | Parent antibody | 10.99 | 1.00 | 0.997 |
|  | vAb1 | 2.45 | 4.48 |  |
| FOLR1-Fc | Parent antibody | 11.85 | 1.00 | 0.972 |
|  | vAb2 | 3.94 | 3.04 |  |
| FOLR1-Fc | Parent antibody | 3.04 | 1.00 | 0.996 |
|  | vAb3 | 0.77 | 3.99 |  |
|  | vAb4 | 1.59 | 1.94 |  |
|  | vAb5 | 2.17 | 1.42 |  |

Example 5: Examination of Binding Affinity of Modified Antibody (vAb) by SPR Assay To measure the binding affinity of the modified antibody vAb1 produced in Example 2 for FOLR1, an SPR assay was performed using a Biacore3000, in the same manner as described in Examples 1-5. The sensorgram was analyzed using the BIAevaluation software, and the $K_D$ value was calculated. The modified antibody vAb1 showed a $K_D$ value of 0.24 nM, which corresponds to a 4-fold higher binding affinity than that of the parent antibody (Table 12). This value is similar to the relative ratio of the values obtained using ELISA.

TABLE 12

Dissociation constants of parent antibody and modified antibody vAb1, measured by SPR

| | Ligand FOLR1 | $k_a$ (1/Ms) | $k_d$ (1/s) | $K_A$ (1/M) | $K_D$ (nM) | Relative Potency | Chi$^2$ |
|---|---|---|---|---|---|---|---|
| Analyte | Parent antibody | 4.19E+05 | 4.01E-04 | 1.05E+09 | 0.96 | 1 | 4.90 |
|  | Modified antibody vAb1 | 6.12E+05 | 1.47E-04 | 4.17E+09 | 0.24 | 4 | 4.86 |

INDUSTRIAL APPLICABILITY

The modified antibody according to the present invention has a sequence in which the antigen-binding site originally possessed by the parent antibody is substituted with an amino acid that better binds to the antigen while preserving the basic structure of the parent antibody. Thus, the modified antibody has increased binding affinity for the antigen. In addition, the antibody or antigen-binding fragment thereof according to the present invention may be used for the prevention or treatment of cancer, and may also be used for diagnosis of disease.

Although the present invention has been described in detail with reference to specific features, it will be apparent to those skilled in the art that this description is only of a preferred embodiment thereof, and does not limit the scope of the present invention. Thus, the substantial scope of the present invention will be defined by the appended claims and equivalents thereto.

Sequence List Free Text
Electronic file is attached.

The invention claimed is:

1. An antibody or antigen-binding fragment thereof that binds specifically to folate receptor-a (FOLR1), said antibody or antigen-binding fragment thereof comprising:
   a heavy-chain variable region of SEQ ID NO: 1 and a light-chain variable region of SEQ ID NO: 32; or
   a heavy-chain variable region of SEQ ID NO: 1 and a light-chain variable region of SEQ ID NO: 33; or
   a heavy-chain variable region of SEQ ID NO: 1 and a light-chain variable region of SEQ ID NO: 34; or
   a heavy-chain variable region of SEQ ID NO: 31 and a light-chain variable region of SEQ ID NO: 2; or
   a heavy-chain variable region of SEQ ID NO: 31 and a light-chain variable region of SEQ ID NO: 32.

2. An antibody-drug conjugate in which a drug is conjugated to the antibody or antigen-binding fragment thereof of claim 1.

3. The antibody-drug conjugate of claim 2, wherein the antibody or antigen-binding fragment thereof is conjugated to the drug via a linker.

4. The antibody-drug conjugate of claim 2, wherein the drug is a chemotherapeutic agent, a toxin, microRNA (miRNA), siRNA, shRNA, or a radioactive isotope.

5. A composition comprising the antibody or antigen-binding fragment thereof of claim 1; or the antibody or antigen-binding fragment thereof of claim 1 conjugated to a drug.

6. A method of diagnosing cancer associated with increased expression of FOLR1, comprising contacting a test cell with the antibody or antigen-binding fragment thereof of claim 1; determining the level of expression of FOLR1 by the test cell by detecting binding of the antibody or antigen-binding fragment thereof to FOLR1; and comparing the level of expression of FOLR1 by the test cell with the level of expression of FOLR1 by a control cell, wherein a higher level of expression of FOLRI by the test cell as compared to the control cell indicates the presence of cancer associated with increased expression of FOLR1.

7. A method for treating cancer in a subject in need thereof, comprising administering an effective amount of the antibody or antigen-binding fragment thereof of claim 1; or the antibody or antigen-binding fragment thereof of claim 1 conjugated to a drug, to the subject, wherein the cancer is FOLR1-overexpressing epithelial cancer.

8. The method of claim 7, wherein the cancer is ovarian cancer, breast cancer, lung cancer, kidney cancer, colon cancer, brain cancer, rectal cancer, cervical cancer, or endometrial cancer.

9. The method of claim 6, wherein the test cell is obtained from an individual suspected of having a cancer associated with increased expression of FOLR1, wherein the cancer is ovarian cancer, breast cancer, lung cancer, kidney cancer, colon cancer, brain cancer, rectal cancer, cervical cancer, or endometrial cancer.

10. The composition of claim 5, which is a pharmaceutical composition and further comprises a pharmaceutically acceptable carrier.

* * * * *